(12) United States Patent
Joseph et al.

(10) Patent No.: US 6,471,689 B1
(45) Date of Patent: Oct. 29, 2002

(54) IMPLANTABLE DRUG DELIVERY CATHETER SYSTEM WITH CAPILLARY INTERFACE

(75) Inventors: Jeffery I Joseph, Penn Valley, PA (US); Marc C. Torjman, Southampton, PA (US)

(73) Assignee: Thomas Jefferson University, Philadelphia, PA (US)

( * ) Notice: Subject to any disclaimer, the term of this patent is extended or adjusted under 35 U.S.C. 154(b) by 83 days.

(21) Appl. No.: 09/639,612

(22) Filed: Aug. 15, 2000

Related U.S. Application Data

(60) Provisional application No. 60/149,027, filed on Aug. 16, 1999.

(51) Int. Cl.[7] .............................................. A61K 9/22
(52) U.S. Cl. .............................. 604/892.1; 604/288.01; 424/424
(58) Field of Search ...................... 604/228.01, 228.02, 604/228.04, 228.03, 891.1, 892.1, 890.1; 424/422, 423, 424, 425, 426

(56) References Cited

U.S. PATENT DOCUMENTS

| 5,041,107 A | * | 8/1991 | Heil, Jr. ................ 604/892.1 X |
| 5,100,392 A | * | 3/1992 | Orth et al. ............. 604/228.02 |
| 5,281,210 A | * | 1/1994 | Burke et al. ............. 604/891.1 |
| 5,800,828 A | * | 9/1998 | Dionne et al. .............. 424/422 |

* cited by examiner

Primary Examiner—Harry B. Tanner
(74) Attorney, Agent, or Firm—Drinker Biddle & Reath LLP

(57) ABSTRACT

The present invention relates to a drug delivery device which is implantable within a mammal and adapted for long-term efficient drug delivery to surrounding tissue. The drug delivery device is part of a drug delivery system that includes a catheter and a drug feed system. The drug delivery device includes a support structure that defines a drug reservoir and a capillary interface which facilitates vascular ingrowth while inhibiting blockage of drug delivery openings in the reservoir.

69 Claims, 21 Drawing Sheets

IMPLANTABLE DRUG DELIVERY CATHETER SYSTEM WITH CAPILLARY INTERFACE

This application claims benefit of Provisional Application No. 60/149,027 filed Aug. 16, 1999.

FIELD OF THE INVENTION

The present invention relates generally to the field of drug delivery systems and, more particularly, to a drug delivery device with a capillary interface that permits tissue ingrowth while facilitating rapid uptake of the drug into the circulation of a mammal.

BACKGROUND OF THE INVENTION

Intravenous (IV), intramuscular, subcutaneous, intraperitoneal and transdermal delivery are the major routes of parenteral drug administration in mammals. Drug absorption from the subcutaneous, transdermal, and intramuscular sites occurs by simple diffusion once a gradient exists from the tissue drug depot to the plasma. The rate of drug absorption is, however, limited by the area of the absorbing capillary membranes (i.e., the capillary density), the portion of open versus closed capillaries, molecular size versus capillary pore size, the skin (transdermal delivery), and the solubility of the substance in the interstitial fluid. While intravenous drug administration circumvents many of these drug absorption problems, it requires that a permanent IV catheter be maintained in a blood vessel. The implanting of IV catheters for an extended period of time typically leads to complications, such as infection and obstruction of the catheter. Also, the delivery of insulin into the peripheral circulation, as opposed to the portal vein, which is the physiologic location for insulin delivery, results in a much lower portal to peripheral insulin concentration ratio compared to normal physiology. (See, Home, PD, "Insulin Therapy", *International Textbook of Diabetes Mellitus*, p. 899–928, 1997).

Another drawback to current methods of parenteral drug administration is that they pose an obstacle to achieving physiologic control and proper management in several debilitating diseases, such as diabetes. For example, the treatment of type I diabetes by subcutaneous insulin administration is unphysiological as absorption and elimination are not rapid enough to effectively maintain normoglycemia. (See, for example, Tarnborlane V W, Sherwin R S, Genel M, and Felig P, "Reduction to Normal of Plasma Glucose in Juvenile Diabetes by Subcutaneous Administration of Insulin with a Portable Infusion Pump", N. Engl. J. Med., 300 (11):574–580, 1979; Hepp K D, "Implantable Insulin Pumps and Metabolic Control", Diabetologia, 37 [Suppl 2]:S 108-S 111, 1994; Hanssen K F, Bangstad H J, Brinchmann-Hansen D, and Dah Jorgensen K, "Blood Glucose Control and Diabetic Microvascular Complications: Long-term Effects of Near-normoglycemia", Diabetic Med., 9:697–705, 1992; "The Diabetes Control and Complications Trial (DCC)", N. Engl. J. Med., 329: 683–689, 1993).

Optimal physiologic insulin therapy requires: 1) delivery of basal levels of insulin between meals and sleep; 2) a prompt increase in insulin levels following meals to prevent hyperglycemia; and 3) a rapid decline toward basal levels after meals to prevent postprandial hypoglycemia. (See, Santiago J V, White N H, and Skor D A, "Mechanical Devices for Insulin Delivery", Recent Advances in Diabetes, Nattrass M, Santiago JV, eds., Edinburgh: Churchill Livingstone. 145–63, 1984; White NH and Santiago J V: "What Can Be Achieved with and What Are the Complications of the Insulin Pump?", Diabetes Mellitus *Achievements and Skepticism,* L'Etang HJC ed . . . Royal Society of Medicine, London, 111–25, 1984).

There are many factors that have been identified as having an influence on subcutaneous drug absorption, such as subcutaneous blood flow, injection location, skinfold thickness, injection depth, orthostatic changes, exercise, ambient temperature, smoking, ketosis, and hypoglycemia. Subcutaneous drug delivery, with either a needle or catheter, can have many diverse complications, such as pain, infection, sore skin, lipodystrophy, subcutaneous abscess formation, redness, eczema, and catheter occlusion. Also, there is a high replacement cost associated with infusion sets.

Currently, approximately 10% of insulin dependent diabetics use Continuous Subcutaneous Insulin Infusion (CSII). The 1992 Diabetes Control and Complications Trial (DCCT) findings in Type I diabetics showed that three or more daily insulin injections, or treatment with an insulin pump, delays the onset or slows the progression of diabetic retinopathy, nephropathy, and neuropathy. CSII is an alternative to multiple dose injections while providing improved blood glucose control and greatest degree of lifestyle flexibility. The pump contains a reservoir of insulin which connects to a catheter inserted by the patient into subcutaneous tissues, usually the abdomen. The pump is programmed to deliver a continuous infusion to provide the patient with an adjustable basal rate for night time and morning. Although CSII has several advantages, there are several problems unique to insulin pump therapy which can lead to deterioration of diabetic control in a matter of hours. Common problems identified in failure to deliver insulin are catheter blockage at the tip due to acute fibrous tissue encapsulation, insulin precipitation, needle misplacement, loss of battery charge and an empty insulin reservoir. As a result, CSII patients experience hyperglycemia and ketoacidosis, especially with the short acting insulin (smaller subcutaneous depot) before the external pump registers an alarm condition of failure to deliver.

There is also a physiologic limitation of subcutaneously infused insulin. The slow absorption prevents a more rapid systemic uptake, even when a needle is left in situ due to slow diffusion from the depot to the surrounding capillaries, dissociation of the hexamer form of insulin to monomer form, and absorption into the pores of the capillary. There is a day to day coefficient of variation of about 30%.

In recent years, implantable catheters have been developed for use as access ports for chemotherapy, nutrition, peritoneal dialysis, and, in some cases, insulin therapy. Examples of such catheters are disclosed in Tenckoff, U.S. Pat. No. 3,685,680 and Hickman, U.S. Pat. No. 4,405,313. These cavity catheters provide intravenous or peritoneal drug delivery but do not provide a tissue interface with neovascularization at the interface. The Tenckoff catheter was developed for use in peritoneal dialysis patients to permit the patients to administer dialysate at home. The Hickman catheter was designed to provide central access to the circulation system within the patient for drug delivery, but has limited long-term effectiveness as an intravascular device. One major drawback to the Hickman catheter is the high incidence of infection and obstruction associated with its use.

To date the only implantable insulin delivery methods have been the implantation of intravenous and peritoneal catheters. It has been reported that 56% of the problems associated with implantable pump use were catheter related. Nonfunctional intravenous catheters all showed an organized blood clot on the tip of the catheter. Angiographic exploration of those catheters, before removal, showed tissue formation dividing the vessel lumen and encapsulating the catheter. Nonfunctional intraperitoneal catheters were examined under laparoscopy and showed intraluminal fibrinous and cellular deposition; dense fibrous deposition around the tip of the catheter; and full or partial encapsulation by omentum. The repair of intraperitoneal catheters by laparoscopic access has yielded a relapse failure rate of 50%.

Another device known as the infusaport is a totally implanted drug delivery catheter system. While this type of device has a lower incidence of infection, it has a high incidence of obstruction and clogging of the catheter after a few months, limiting its long-term use. A variety of companies make infusaports, such as Baxter Healthcare.

With regard to insulin therapy it is currently thought that catheters are the weakest link in the chain of the components of a closed loop system. (See, Selam J L: "Development of Implantable Insulin Pumps: Long is the Road", Diabetic Med., 5 (8):724–733, 1988). The International Study Group on Insulin Infusion Devices (ISGIID) registry has reported that 56% of the problems associated with insulin pump use are catheter-related. (Knatterud G, Fisher M: "Report from the International Study Group on Implantable Insulin Delivery Devices", ASAIO Transactions, 34 (2):148–149, 1988).

According to the literature, it is clear that catheter development is very limited for drug delivery and should be a priority for the future development of closed loop insulin delivery. (Selam J L and Charles M A, "Devices for Insulin Administration", Diabetes Care, 13:9, 1990; Renard E, Baldet P, Picot M C, Jacques-Apostol D, Lauton D, Costalat G, Bringer J, and Jaffiol C., "Catheter Complications Associated with Implantable Systems for Peritonea] Insulin Delivery", Diabetes Care, 18:3,300–306, 1995; Von Recum A F, "Applications and Failure Modes of Percutaneous Devices: A Review", J. Biomed. M. Res., 18:323–336, 1984). Only one study, by E. S. Wilkins (Wilkins E S, "Tissue Reaction to Intraperitoneally Implanted Catheter Materials", J. Biomed. Env,., 13, 1991), has been found which investigated the tissue reaction to intraperitoneally implanted catheters with tips modified by application of various surface treatments. Although the methodology was brief, it is clear that this investigator used very large pore sizes on the coatings of the catheter tips. The findings of that study did not address functionality of their device after implantation and, therefore, were inconclusive with regard to drug delivery.

It is now well known that the implantation of a biomaterial triggers a foreign body response characterized by inflammation and encapsulation of the foreign body. When using nonreactive materials, this process is transient and lasts a few weeks. The classical foreign body response is the formation of a primary layer of macrophages and giant cells over the implant. This primary layer is then overlaid by several layers, approximately 30–100 microns thick, of fibroblasts. (See, Brauker J H, Carr-Brendel V E, Martinson L A, Crudele J, Johnston W D, Johnson R C, "Neovascularization of Synthetic Membranes Directed by Membrane Architecture", J. Biomed. Materials Res., 29:1517–1524, 1995). One benefit of the encapsulation of the foreign body is that its dislodgement is inhibited. However, encapsulation of conventional drug delivery devices provides a mechanical barrier that slows or inhibits the movement of drug to surrounding capillaries.

A need, therefore, exists for an improved implantable device and system for dispensing drugs within a mammal.

SUMMARY OF THE INVENTION

An object of the present invention is to provide an implantable drug delivery device which facilitates drug absorption into a mammal.

This and other objects and advantages of the invention are provided by the drug delivery device and system according to the present invention. The drug delivery device is adapted for implantation into a mammal for drug delivery to a prescribed location. The drug delivery device includes a support structure adapted to receive a flow of drugs. The support structure defines a drug reservoir and has openings formed in it which permit drugs to flow out of the support structure and into the mammal.

A capillary interface is disposed about the support structure and includes an outer portion which is adapted to facilitate the ingrowth of vascular tissue. The capillary interface also includes an inner portion which is adapted to inhibit the ingrowth of vascular tissue while permitting the flow of drugs from the support structure out through the capillary interface.

In one embodiment, the outer portion is an outer membrane pore structure and the inner portion is an inner membrane pore structure. The pores on the outer membrane pore structure are larger than the pores on the inner membrane pore structure.

The drug delivery device is designed to operate as part of a drug delivery system. The drug delivery system also includes a catheter attached to the drug port on the drug delivery device for channeling drugs into the drug delivery device. The catheter is in fluid communication with a drug feed device that includes a drug supply and a pump. The pump is adapted to produce a positive pressure flow of drugs out of the drug supply, through the catheter and into the drug reservoir. A processor is attached to the pump and controls delivery of drugs.

The present invention, which is at times referred to herein as the Capillary Interface Drug Delivery Device (CID3), effectively addresses the significant limitations of subcutaneous, transdermal, intramuscular, intraperitoneal, or IV drug therapies. The uniqueness of the present device as a drug delivery system resides in the use of biocompatible three-dimensional scaffolds to generate a capillary interface on a drug delivery device. The capillary interface facilitates rapid uptake of a drug into the circulation of a human or animal.

The foregoing and other features and advantages of the present invention will become more apparent in light of the following detailed description of the preferred embodiments thereof, as illustrated in the accompanying figures.

BRIEF DESCRIPTION OF THE DRAWINGS

For the purpose of illustrating the invention, the drawings show a form of the invention which is presently preferred. However, it should be understood that this invention is not limited to the precise arrangements and instrumentalities shown in the drawings.

FIGS. 14a and 14b are cross sections showing alternate scaffold arrangements for the catheter in FIG. 14.

FIG. 14c is a needle introducer for inserting the catheter of FIG. 14 into the skin of a patient.

FIGS. 15a and 15b are cross sections of the catheter of FIG. 15.

DETAILED DESCRIPTION

Figure 1:
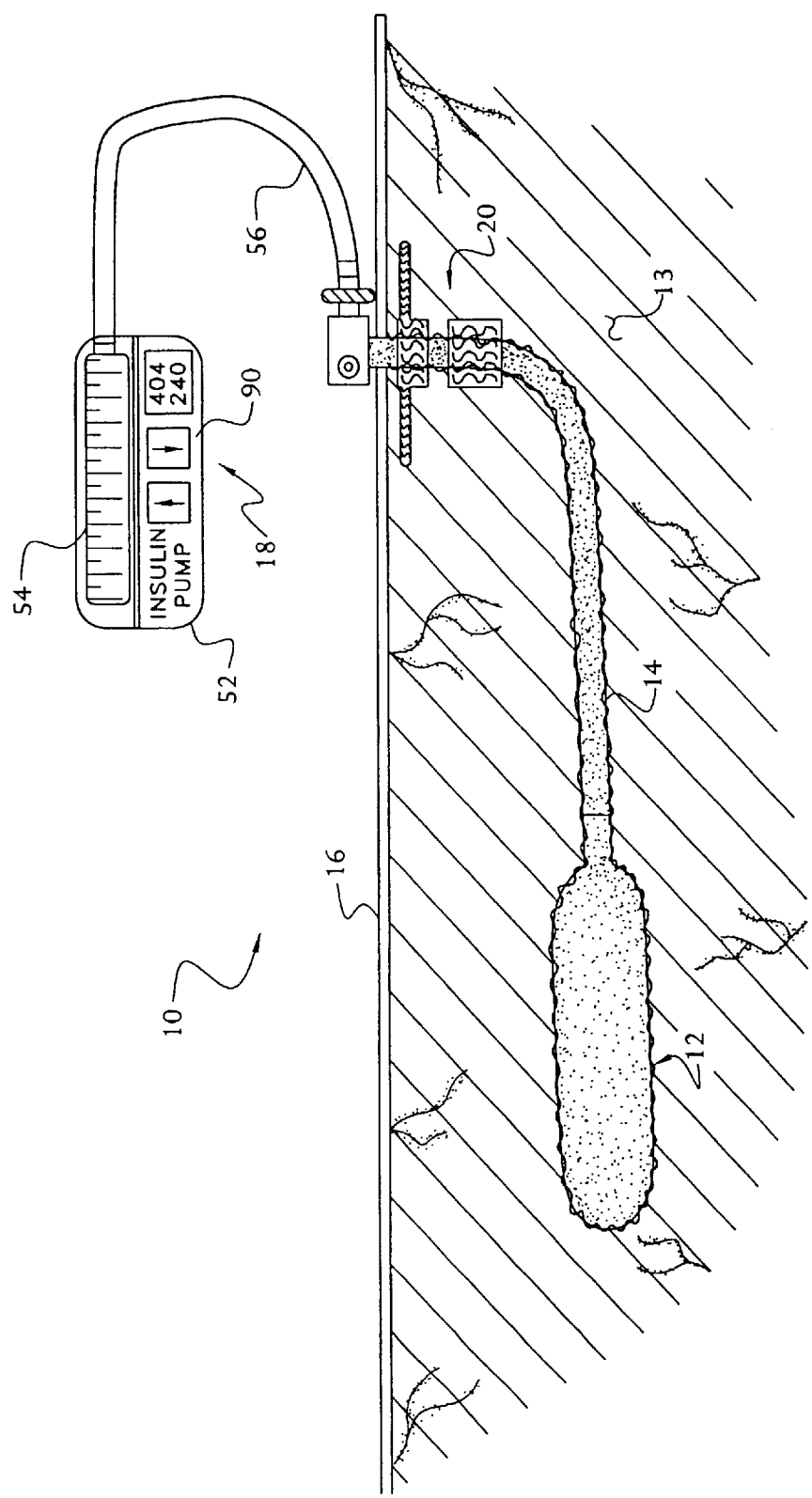
FIG. 1 is a schematic view of an implantable drug delivery catheter system according to the present invention.

While the invention will be described in connection with one or more preferred embodiments, it will be understood that it is not intended to limit the invention to those embodiments. On the contrary, it is intended that the invention cover all alternatives, modifications and equivalents as may be included within its spirit and scope as defined by the appended claims.

Certain terminology is used herein for convenience only and is not to be taken as a limitation on the invention. Particularly, words such as "upper," "lower," "left," "right," "horizontal," "vertical," "upward," and "downward" merely describe the configuration shown in the figures. Indeed, the components may be oriented in any direction and the terminology, therefore, should be understood as encompassing such variations unless specified otherwise.

Referring now to the drawings, wherein like reference numerals illustrate corresponding or similar elements throughout the several views, the present invention is illustrated in various embodiments that are currently contemplated. Those skilled in the art would readily be capable of modifying these embodiments to practice the invention in alternate ways within the scope of the claims. Also, while the following discussion concentrates on use of the present invention for insulin delivery, it is not limited to solely that type of drug. On the contrary, the present invention can be used for any type of drug that benefits from systemic uptake.

It is well known that currently intensive insulin treatment methods are ineffective in the general population for long-term normalization of glycosylated hemoglobin. These observations are derived from the concept that multiple intermittent subcutaneous injections are highly artificial. The subcutaneous depot or delivery site is associated with too many insulin absorption variables to be successful. The present invention, however, addresses the deficiencies of the prior art drug delivery systems by providing an innovative drug delivery device and system which gives a more rapid insulin delivery to effectively suppress glucose surges, reducing mortality and morbidity resulting from poor glucose control.

The present invention also minimizes the risk of infection and the issue of frequent disconnects by the incorporation of a dacron (or other biomaterial) structure below the skin surface and/or etching of the entire catheter surface. This technique provides tissue anchoring and the prevention of bacterial migration along the catheter.

The present invention also allows the patient greater flexibility of lifestyle, freedom of movement, and the ability to carry out physical activity in a more natural and comfortable manner. The present invention eliminates the need for frequent injections and the pain associated with multiple daily needle injections, skin irritation, mental anguish suffered by patients having difficulty controlling or maintaining the physiologic parameters pertaining to their clinical condition.

Referring now to FIG. 1, one embodiment of a drug delivery catheter system 10 according to the present invention is shown as it is intended to be located within a mammal. The drug delivery catheter system 10 includes a capillary interface drug delivery device 12, or CID₃, that is attached to or formed on or part of a catheter 14. As will be discussed in more detail below, the drug delivery device 12 is located within the connective tissue 13 of a mammal, below its skin 16. A portion of the catheter 14 is also positioned within the mammal. One end of the catheter 14 extends out from the skin 16 and, preferably, is adapted to be connected or is physically connected to a drug feed device 18.

A retaining device 20 is attached to the catheter 14 and located under the skin 16 when the catheter 14 is implanted. The retaining device 20 is adapted to secure the catheter 14 within the mammal to prevent inadvertent removal, and to minimize the spread of infection.

For the sake of simplicity, the following discussion will concentrate on the applicability of the present invention within a human. However, it is contemplated that the device can be utilized on any mammal.

Figure 2:
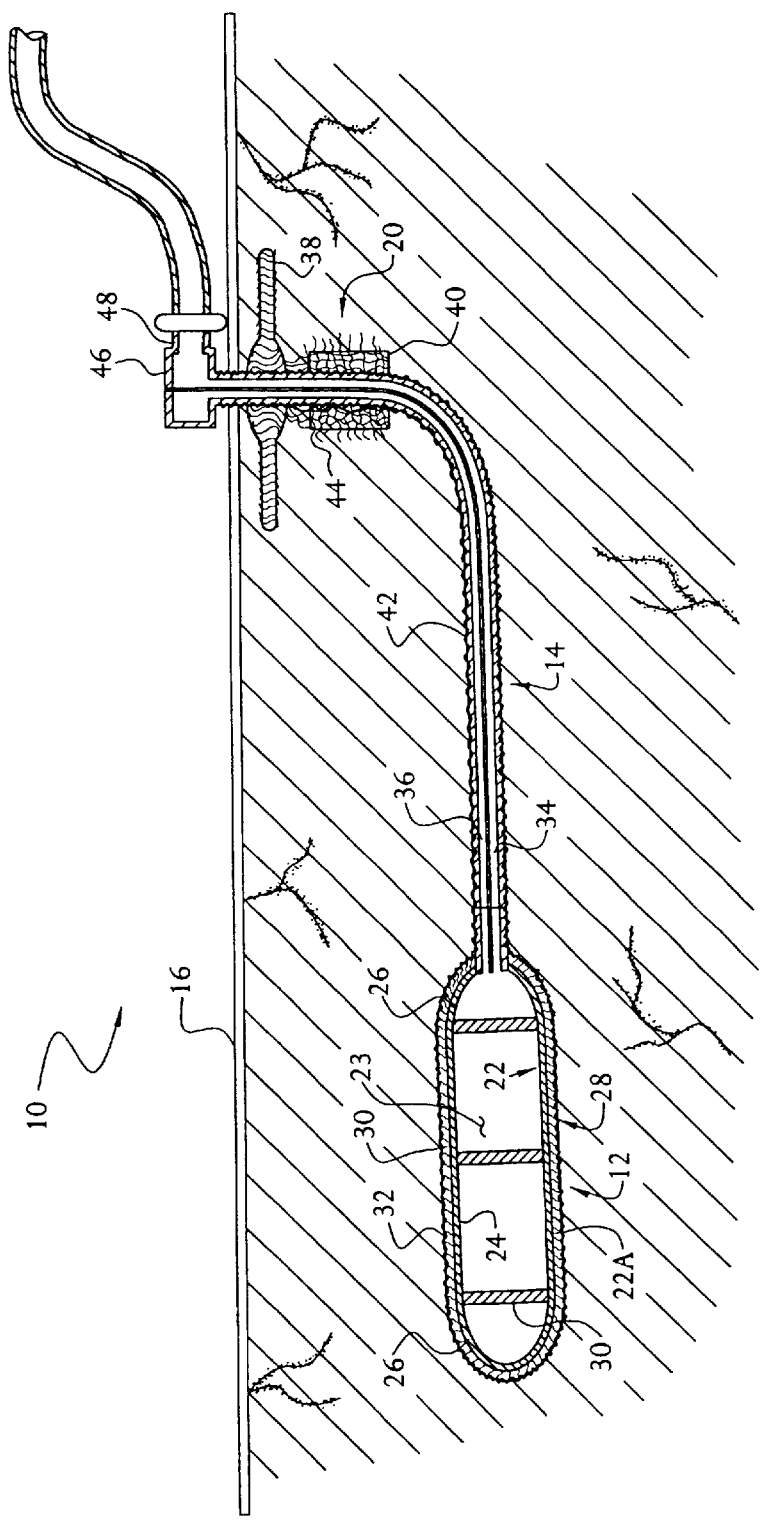
FIG. 2 is a cross-sectional view of the implantable drug delivery catheter system of FIG. 1.
Figure 3:
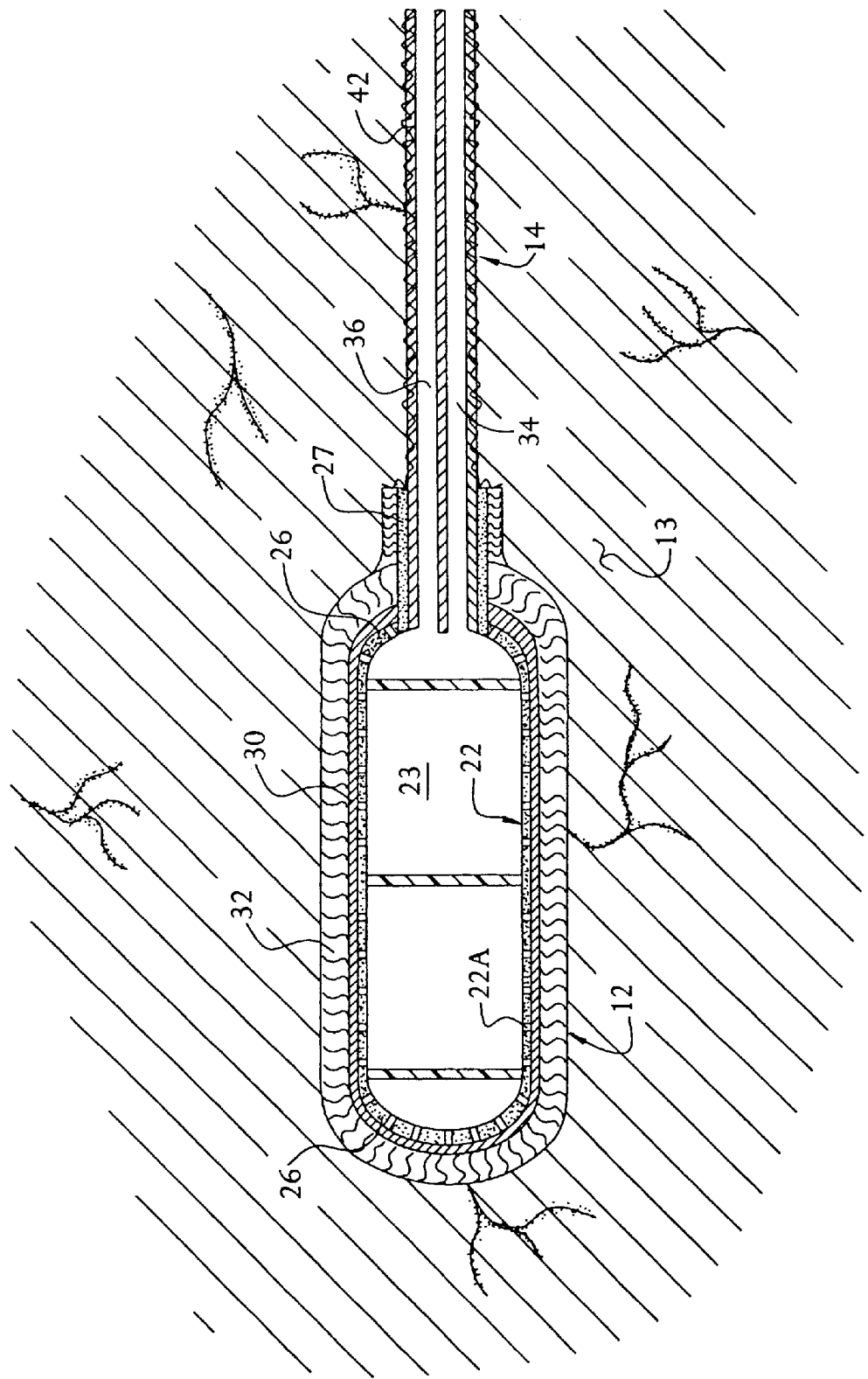
FIG. 3 is an enlarged view of an implantable drug delivery device.
Figure 4:
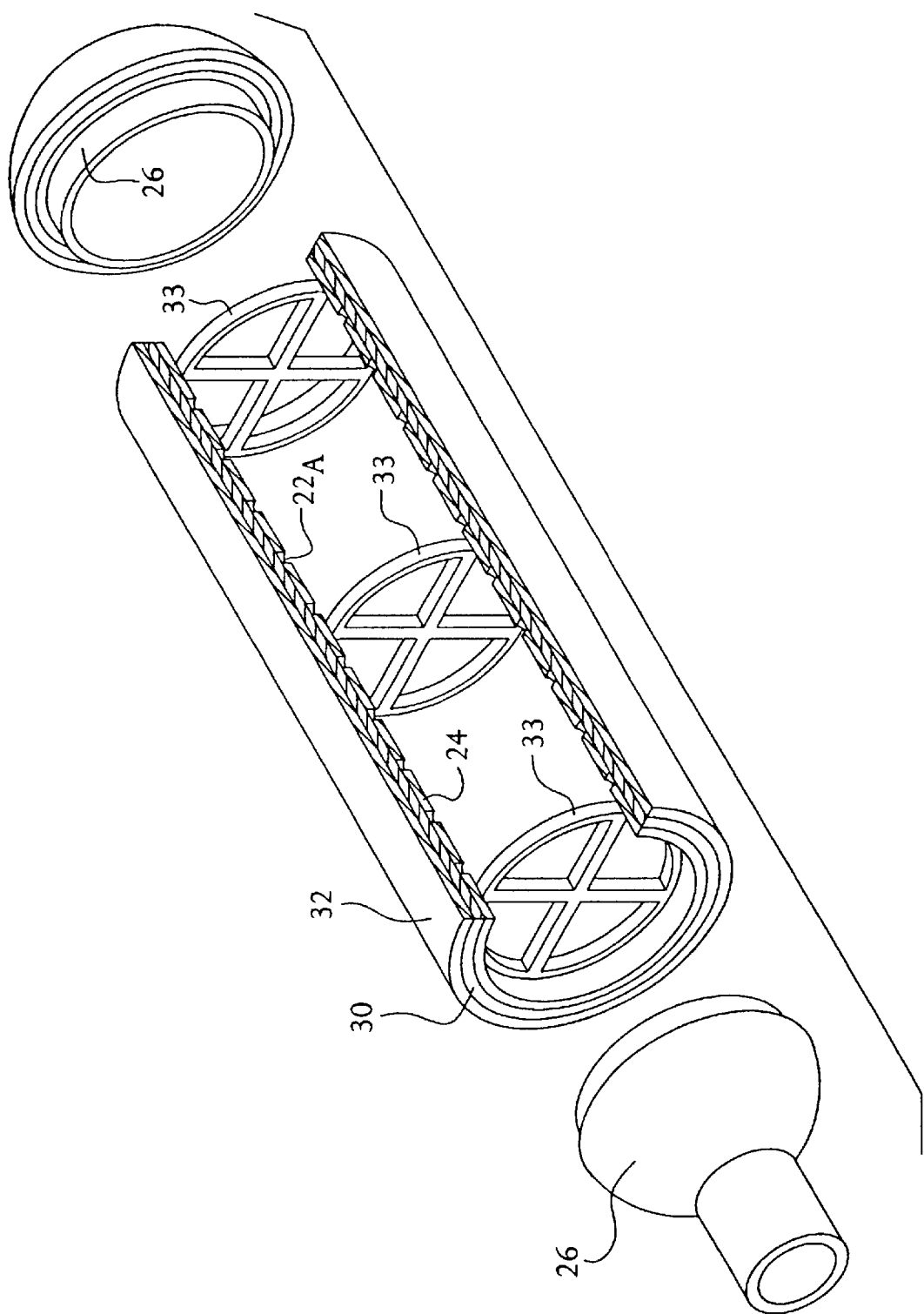
FIG. 4 is an exploded view of one embodiment of an implantable drug delivery device.

Referring now to FIGS. 2 and 3, which illustrate cross-sectional views of one embodiment of the drug delivery device, 12 and the catheter 14. In this embodiment, the drug delivery device 12 includes an internal support structure 22 made from a biocompatible material, such as titanium or plastic. The internal support structure 22 is formed with a plurality of openings or perforations 22A to permit passage of drugs from inside to outside the structure. The openings can be formed at a prescribed location on the support structure 22 or can be formed completely around it. As will be discussed in more detail below, the internal support structure 22 forms a reservoir or cavity 23 for containing and dispersing drugs. The internal support structure 22 is preferably designed to withstand the anticipated loads that will be applied, such as internal pressures exerted by tissues, interstitial fluid, and higher external pressures applied to the body, e.g., external pressures applied in contact sports.

In one preferred embodiment, the support structure 22 of the drug delivery device 12 has a cylindrical shell or housing 24 with smooth semi-hemispherically shaped proximal and distal ends 26. The shape of the ends 26 is designed to avoid any tissue reaction of the chronic type and to minimize encapsulation. The proximal and distal ends 26 can be formed integral with or separately attached to the main cylindrical housing 24 of the drug delivery device 12. As shown, the proximal end includes a port 27 designed to permit the passage of fluid into the drug reservoir 23. In an alternative embodiment, the support structure 22 can be formed as a cage or frame structure.

A tissue engineered capillary interface 28 is formed on the support structure 22. The capillary interface 28 includes an inner membrane pore structure or layer 30 and an outer membrane pore structure or layer 32. The inner membrane pore structure 30 preferably has pore cell sizes between approximately 100 Angstroms to 0.8 $\mu$m with a preferred cell size of 0.02 $\mu$m The inner membrane pore structure 30 thickness is between about 2 $\mu$m to about 200 $\mu$m with a preferred thickness of about 100 $\mu$m The outer membrane pore structure 32 preferably has larger pore cell sizes than the inner pore cells. The outer membrane pore cells preferably range in size from approximately 0.02 $\mu$m to approximately 300 $\mu$m. More preferably, the cell sizes for the outer pore membrane structure 32 range from about 2 $\mu$m to about 100 $\mu$m with the preferred cell size being about the 50 $\mu$m. The larger pores on the outer membrane pore structure 32 facilitate tissue growth into the capillary interface 28. The smaller cells on the inner membrane pore structure 30 inhibit tissue growth and cell penetration into the drug reservoir 23. The outer membrane pore structure 32 preferably has a thickness of between 10 $\mu$m to about 1000 $\mu$m, with the most preferred thickness being about 1000 $\mu$m.

Also, the outer membrane pore structure 32 preferably has a porosity of between 70 to about 95 percent, and, more preferably, about 90 percent porosity. The open pores on the outer membrane pore structure 32 are preferably in alignment with the open pores of the inner membrane pore structure 30 to facilitate drug delivery.

The support structure 22 forms the membrane layers 30, 32 into a three-dimensional interconnecting pore scaffold structure which promotes tissue growth and neovascularization for drug delivery. It should be noted that the support structure 22 and membrane layers 30, 32 may be located on any part of the catheter or make up either a portion or the entire length of the drug delivery device. The membranes layers 30, 32 may be composed of single or multiple layers of biocompatible materials, including, but not limited to, hydrogels, poly (2-hydroxyethyl methacrylate, pHEMA), hydroxyethyl methacrylate. (HEMA), polyacrylonitrile-polyvinyl chloride (PAN-PVC), polymers, polytetrafluoro-ethylene (PTFE), expanded polytetrafluoroethylene (ePTFE), polypropylene, high density polyethylene, polyurethane, polyester (Dacron), polyvinyl chloride, polyvinyl alcohol, acrylic copolymers, polysulfone, nylon, polyvinyl difluoride, polyanhydrides, silicone, polycarbonate, cellulose acetate, mixed ester cellulose, collagen, fibrin, poly(1-lysine), poly (L-lactic acid), hydroxyethylmetharcrylate, protein polymers, peptides polymers, hydroxyapeptite, alumina, zirconia, carbon fiber, aluminum, calcium phosphate, titanium, titanium alloy, nintinol, stainless steel, and CoCr alloy. The outer membrane 32 can be made from the same or different material than the inner membrane 30.

The membranes may be modified to further optimize drug delivery, such as by adding polyethylene oxide (PEO), heparin, albumin, tissue growth factors, angiogenic growth factors, and other interstitial tissue matrix substances, anti-inflammatory medications, and anti-rejection medications that promote and maintain healthy vascular tissue throughout the interconnecting pore structure, while minimizing the deposition of matrix proteins, fibrin, or collagen within the inner pore structure.

Angiogenic growth factors which may be used in the membranes include, but are not limited to, Basic Fibroblast Growth Factor (bFGF), (also known as Heparin Binding Growth Factor-II and Fibroblast Growth Factor II), Acidic Fibroblast Growth Factor (aFGF), (also known as Heparin Binding Growth Factor-I and Fibroblast Growth Factor-I), Vascular Endothelial Growth Factor (VEGF), Platelet Derived Endothelial Cell Growth Factor BB (PDEGF-BB), Angiopoietin-1, Transforming Growth Factor Beta (TGF-Beta), Transforming Growth Factor Alpha (TGF-Alpha), Hepatocyte Growth Factor, Tumor Necrosis Factor-Alpha (TNF-Alpha), Angiogenin, Interleukin-8 (IL-8), Hypoxia Inducible Factor-I (HIF-1), Angiotensin-Converting Enzyme (ACE) Inhibitor Quinaprilat, Angiotropin, Thrombospondin, Peptide KGHK, Low Oxygen Tension, Lactic Acid, Insulin, and Growth Hormone.

Extracellular matrix proteins (ECM) placed within the outer membrane pore structure provide cellular support, cellular polarity, cell orientation signals, and points of cellular adhesion to enhance vascular tissue ingrowth and angiogenesis. Signaling occurs through transmembrane integrin molecules that connect the external environment to the internal cytoskeleton. ECM proteins include, but are not limited to, collagens, laminins, fibronectins, proteoglycans, vitronectins, fibrin, and albumin. Living cells (muscle, adipose, liver, kidney, ect.) placed within the outer membrane structure produce an extracellular matrix that promotes cellular adhesion and migration to enhance vascular tissue ingrowth and angiogenesis. Signaling occurs through transmembrane integrin molecules that connect the external environment to the internal cytoskeleton.

The higher porosity of the outer membrane 32 will produce tissue neovascularization into the membrane 32. (See, Mikos A. G., Sarakinos G., Leite S. M., Vacanti J. P., and Langer R., "Laminated Three-dimensional Biodegradable Foams for Use in Tissue Engineering", Biomaterials, 14, 323–330, 1993; Brauker J H, Carr-Brendel V E, Martinson L A, Crudele J, Johnston W D, Johnson R C: "Neovascularization of Synthetic Membranes Directed by Membrane Microarchitecture", J. Biomed. Materials Res., 29:1517–1524, 1995). The smaller pore size of the inner membrane 30 serves a protective function, preventing cellular penetration and capillary and tissue ingrowth into the drug delivery reservoir 23. Polymers such as PHEMA, PHEMA-co-MMA and PTFE possess the necessary characteristics to form the inner membrane 30. Since the average capillary diameter is from four to nine micrometers, the pore size on the outer membrane layer 32 preferably exceeds 3 micrometers. The large pores of the outer membrane provide a support surface which allows ingrowth and maintenance of a capillary network immediately adjacent to the inner protective membrane 30 and proximate the drug reservoir 23. The inner membrane pore structure 30 prevents the openings/perforations 22A in the support structure 22 from being obstructed by the deposition of protein, carbohydrate, fat, or the ingrowth of migratory cells or the acellular matrix of the interstitial tissues.

This unique engineering of the membrane bi-layer promotes the formation of a capillary network immediately above the inner membrane, while simultaneously preventing tissue ingrowth, protein deposition, and insulin crystallization within the lumens of the smaller pores. The polymers listed above possess the necessary characteristics for inner membrane function. Diffusion of insulin through the inner membrane is influenced by membrane thickness, surface area, pore density, and pore size. The thin inner membrane (2 to 200 micrometers thick) controls insulin diffusion from the drug delivery reservoir to the outer membrane. Drug delivery to the outer capillary network will be dependent upon positive pressure from the drug infusion pump. These design characteristics of the drug delivery device make it possible to deliver drugs in a more physiologic fashion by permitting rapid uptake of the drug via the capillary interface (large pores) when positive pressure from the pump is applied. When the pump is turned off drug delivery is rapidly terminated, with no drug depot forming within the drug delivery device 12. Hence, the inner membrane provides a dual function by serving as both a rate limiting and protective structure.

In one embodiment of the invention, the drug delivery device 12 has an internal diameter of between about 1 mm and about 100 mm with a length of between about 3 mm and about 400 mm. However, it should be readily apparent that the size of the drug delivery device 12 will vary depending on the surrounding anatomy and physiology demands of the human or animal. In one preferred embodiment, the support structure 22 of the drug delivery device 12 is reinforced with one or more internal support members 33, which prevent the support structure 22 from collapsing. The internal support members 33 can be any suitable shapes, such as circular rings or longitudinal laminates. The internal support members 33 are designed to permit drugs to pass throughout the drug reservoir 23. The volume of the drug reservoir 23 will vary depending on the size of the drug delivery device 12. For example, in one embodiment, the drug reservoir 23 is between about 10 microliters to about 5 milliliters, with a preferred volume of about 0.25 milliliter. The volume would be selected based on several factors, including the size of the mammal, the clinical indication and the pathology. These factors would assist in determining the drug selection and concentration necessary for the indicated therapy.

The catheter 14 is attached to the proximal end 26 of the drug delivery device 12 so as to permit fluid communication between the catheter 14 and the drug reservoir 23. More particularly, the end of the catheter 14 is inserted into the port 27 on the support structure 22 such that the catheter's lumen can channel fluid into the drug reservoir 23. In one embodiment of the invention, the catheter 14 is preferably a double lumen catheter, which permits drug delivery to the drug reservoir 23 through one lumen 34, and flushing of the reservoir 23 with the other lumen 36. The dimensions of this double lumen catheter will be such that a segment of tubing between approximately 0.5 cm and 3 cm in length (or longer, if necessary) will be tunneled out from the implantation site to the skin surface 16. It is desirable to form the catheter 14 longer than necessary to permit the catheter 14 to be coiled near the skin in order to provide an added degree of slack. The slack helps prevent dislodging of the drug delivery device 12 and disrupting the tissue engineered interface 28 when excessive skin stretching, pulling, or tugging of the catheter 14 occurs. The internal diameter of each lumen 34, 36 will be about 0.1 mm to about 10 mm Of course, in a double lumen catheter, the diameters of the two lumens can differ. One of the factors determining the internal diameters of the lumen is the type of drug and the drug preparation.

The catheter 14 is preferably made of elastomeric polymers of medical grade, such as silicon rubber, polyvinyl chloride, polyethylene or other materials, which are suitable for implantation.

Figure 5:
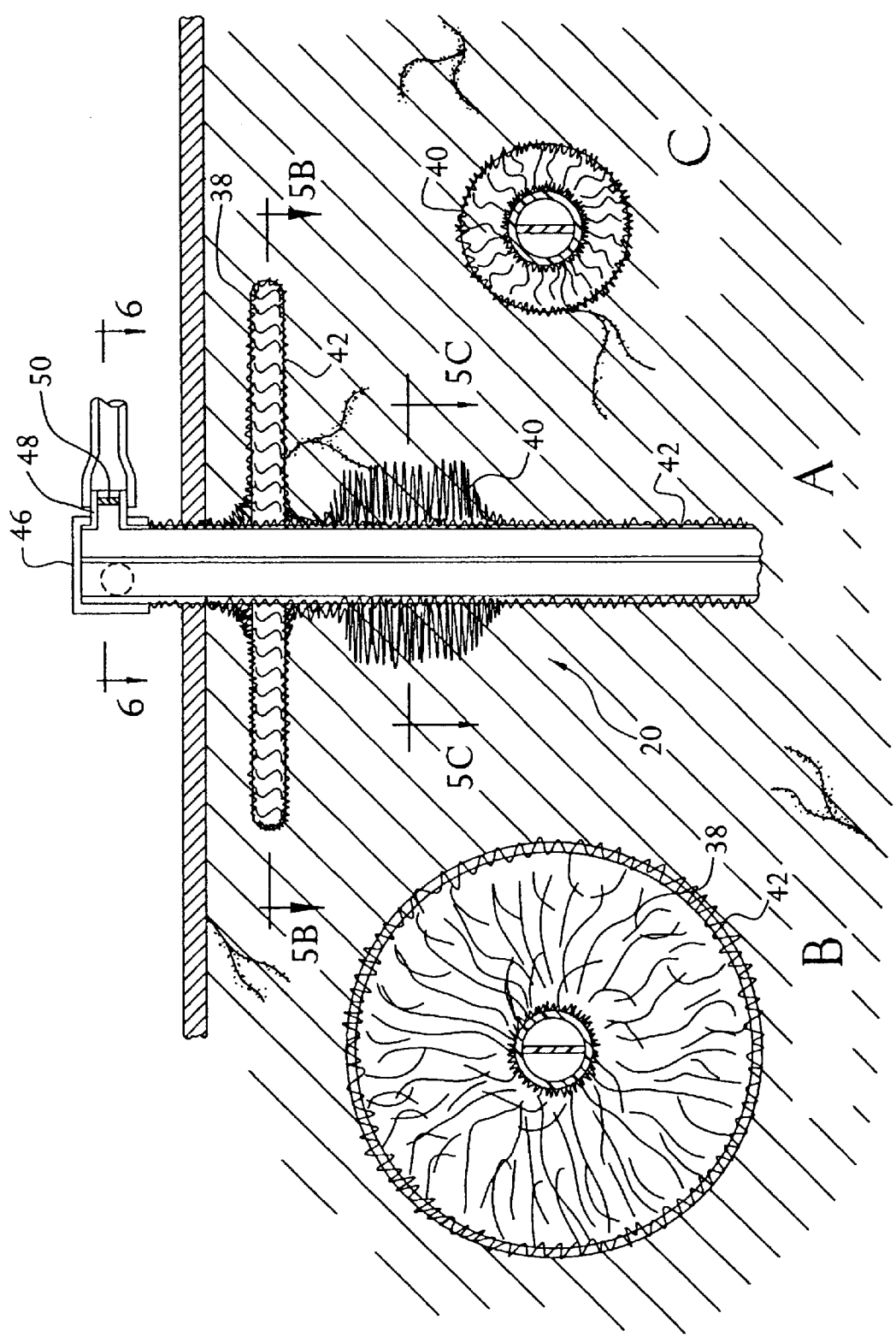
FIG. 5 is an enlarged view of a retaining device for securing an implantable catheter under the skin of a mammal.

The retaining device 20 in the embodiment of the invention shown in FIGS. 5A–5C preferably includes an anchor 38 that is mounted around the catheter 14 below the skin surface 16. The anchor 38 is located close to the skin and preferably has a diameter considerably wider than the diameter of the catheter 14. The anchor 38 is preferably large and strong enough to prevent catheter dislodgment and dissipate traction forces, such as those that occur from pulling on the catheter, over a wide area of cutaneous and subcutaneous tissue. In the illustrated embodiment, the anchor 38 is in the shape of a disc and is located just below the surface of the skin 16. The disc preferably has a diameter between about 0.5 cm and about 10 cm. It is contemplated, however, that the anchor 38 can be formed in any suitable shape or size as required. The anchor 38 is preferably made from polymers, such as dacron, or other suitable biomaterials that may be impregnated with an antibiotic to prevent bacteria] infection.

The anchor 38 and the catheter 14 both preferably have an outer layer 42 of open pore structure formed on them, such as a velour-like layer, to facilitate ingrowth of vascular tissue. Alternatively, the outer surface of these components can be etched to form a three-dimensional, open pore structure, which permits tissue ingrowth. Accordingly, following subcutaneous implantation within the connective tissue layer 13, healthy vascular tissue 44 will grow into the open pore structure of the anchor 38 and catheter wall 14, anchoring the catheter 14 along it's entire course and providing a further mechanical barrier to the distal spread of infection.

With regard to catheter attachment at the skin, it is important to prevent epithelial downgrowth along the catheter while promoting attachment of the epithelial cells to the catheter surface making a strong mechanical bond. This is achieved by creating a porous surface on the percutaneous segment of the catheter which has been shown to promote epithelial adhesion and limit downward epithelial migration. (See, Squier, C A, Collins, P., "The Relationship Between Soft Tissue Attachment, Epithelial Downgrowth and Surface Porosity", *Journal of Periodontal Research*, 16:434–440, 1981).

A cuff 40 may incorporated into the retaining device 20 and is preferably located below the anchor 38. The cuff 40 operates to further inhibit the passage of bacteria along the catheter 14, thereby reducing the chance of infection for the patient. The cuff 40 is located around the outer periphery of the catheter 14 and is preferably made from dacron or similar material to facilitate tissue ingrowth for further anchoring the catheter 14. The cuff 40 may be impregnated with an antibiotic to prevent bacterial infection and interstitial matrix compounds to promote tissue integration and adhesion.

Figure 6:
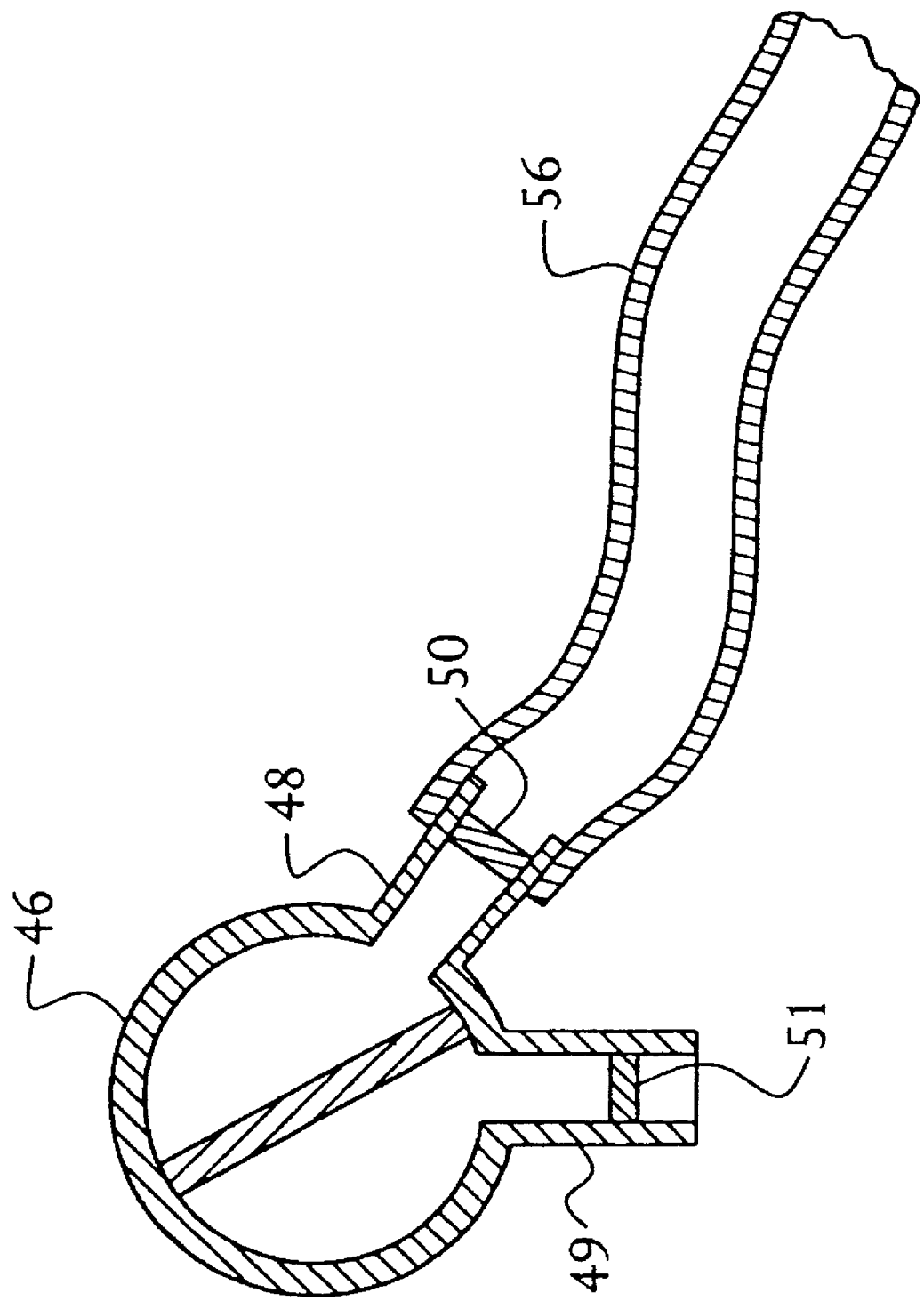
FIG. 6 is a cross-sectional view of an end cap on an implantable catheter.

As discussed above, the proximal end of the catheter 14 extends out of the skin 16. Referring now to the figures and, in particular, FIGS. 5 and 6, an end cap 46 is formed on the distal end of the catheter 14. The end cap 46 can be separately attached to the catheter 14, or may be formed as an integral part of the catheter 14. The end cap 46 includes at least one and, more preferably at least two ports 48. If a single lumen catheter 14 and single port end cap 46 is used, the port 48 connects to the lumen to permit delivery of drugs from a drug supply to the drug delivery device 12. If a dual lumen catheter 14 is used, the end cap 46 preferably includes two ports, both communicating with the drug delivery device 12. In this embodiment, one port 48 communicates with one lumen and is connected to the drug supply. The second port (identified in FIG. 6 by the numeral 49) communicates with the second lumen leading to the drug delivery device 12. The second port 49 preferably includes a one-way pressure relief valve 51. An antibacterial filter (not shown) can also be attached to or incorporated into either the second port 49 or the first port 48. The second port 49 operates as a cleansing port permitting flushing of the drug delivery device 12 and the catheter 14. The pressure relief valve 51 prevents excessive pressure that could lead to tissue damage or cause inadvertent capillary delivery of drug from developing within the system.

In one embodiment of the invention, the end cap 46 is a luer lock connector, which rests on a flat smoothly shaped collar and is attached with a connecting assembly. The luer lock connector is designed as a sealed compartment from which disposable external tubing is connected between the catheter 14 and a pumping device. Luer lock connectors are typically made from light durable plastic and are well known in the art. Hence, no further discussion is needed.

A filter 50 is preferably incorporated into the end cap 46. The filter 50 is preferably an antibacterial filter designed to prevent contaminants from passing into the catheter 14. It should be readily apparent that the filter 50 need not be incorporated directly into the end cap 46. Instead, the filter 50 can be removably attached to the end of the port 48, or may be located in the external tubing that feeds the drugs to the end cap 46.

As discussed above, the drug delivery system 10 also includes a drug feed device 18. The drug feed device 18 is connected to at least one port 48 of the end cap 46. The drug feed device 18 includes a drug delivery infusion pump 52 and a drug storage reservoir 54 (shown in FIG. 1). The infusion pump 52 is operative for delivering a predetermined amount of drug to the drug delivery device 12. The storage reservoir 54 may include a scale for visually indicating the level of drug remaining within the storage reservoir 54. The storage reservoir 54 may be a separate cartridge that is inserted into the drug delivery system 10. Drug delivery infusion pumps and reservoirs are well known in the art, and are sold by many manufacturers, including MiniMed, Disetronic and Animas.

A processor 90 is preferably located within the drug deliver system 10 and controls the pump 52. The processor 90 is programmed to dispense drugs in a prescribed manner. Processors for controlling drug delivery are well known in the art and, therefore, no further discussion is needed.

The storage reservoir 54 is connected to the port 48 with conventional tubing 56. A quick disconnect attachment 58 is used to attach the tubing 56 to the port 48. The attachment is preferably designed to withstand only forces detrimental to the internal capillary interface. For example, forces near 1 kg can typically be generated by excessive pulling or tugging of the catheter. These forces are estimated to be equivalent to pulling that will stretch the skin beyond its normal elastic property and also beyond the coiled slack of the catheter under the skin. To prevent excessive stretching and any resulting damage to the skin, the quick disconnect attachment 58 is designed to disconnect the tubing 56 from the port 48. One suitable quick disconnect that could be used with the present invention includes a male portion of the attachment that has a tapered tip designed to engage with a female portion of the attachment. The male portion slides into the female portion. Stopping rings can be formed on one or both portions and limit that sliding of the male portion into the female portion.

The tubing 56 and quick disconnect attachment 58 are preferably made from durable, non-toxic, biologically neutral and biocompatible materials which can withstand sterilization and are insensitive to medication, as well as non-absorbent. The tubing 56 preferably has an internal diameter of between about 0.2 mm and about 10 mm. An additional antibacterial filter (not shown) may be incorporated into the tubing 56.

The drug reservoir cartridge 54, external tubing 56, and antibacterial filter are preferably supplied as a sterile, closed unit and connected to the antibacterial filter 50 and port 48 using conventional aseptic techniques.

Figure 7:
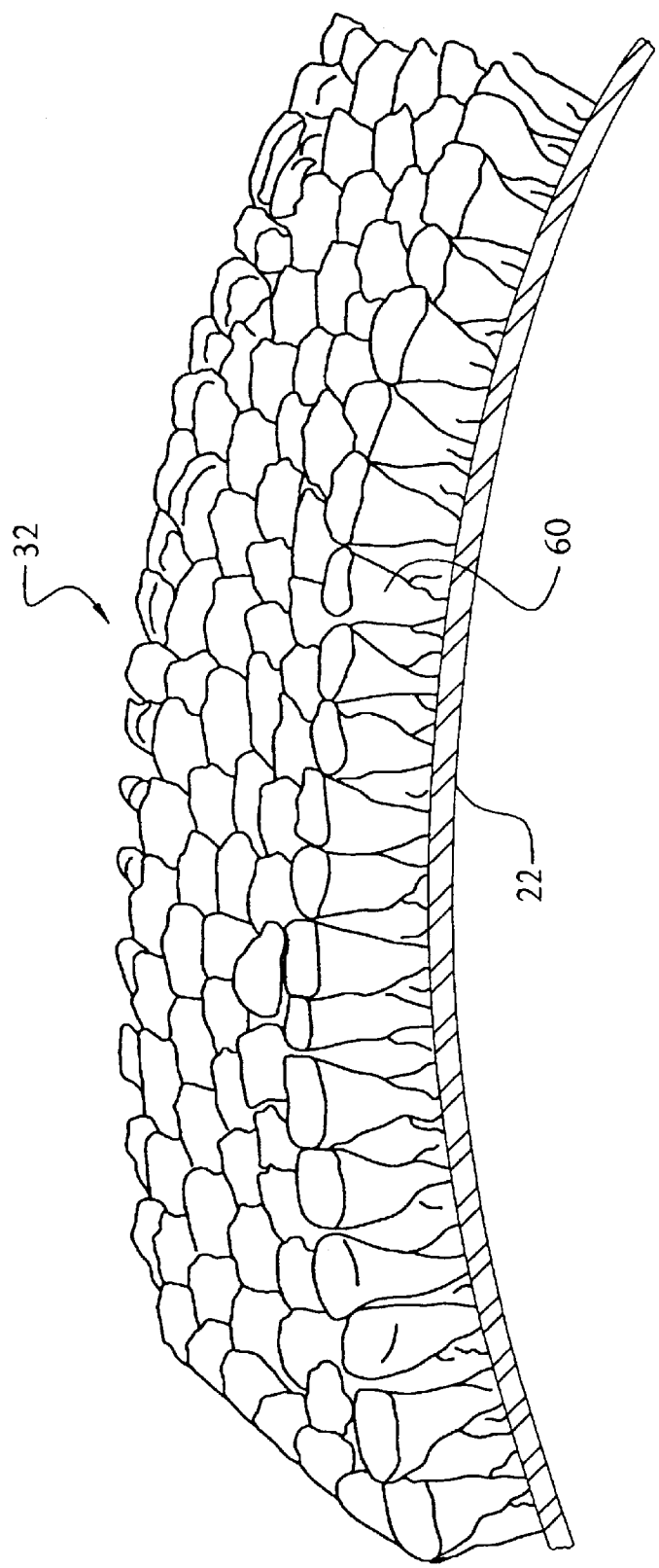
FIG. 7 is an enlarged view of an alternate embodiment of an outer tissue scaffold membrane for use in an implantable drug delivery catheter device according to the present invention.

Referring now to FIG. 7, an alternate embodiment of the outer layer 32 is shown in enlarged detail. In this embodiment, the outer layer 32 includes tapering elements 60 with large pores located on the outer surface and small pores located on the inner surface. The tapering pore structure 60 defines a three dimensional matrix of interconnected pores. In this embodiment, a separate inner layer 30 is not needed in the capillary interface 28. Instead, the small pores of the tapering elements 60 have a diameter which inhibits tissue growth. The end of the tapering elements with the small pores is mounted on the support structure 22.

Figure 8:
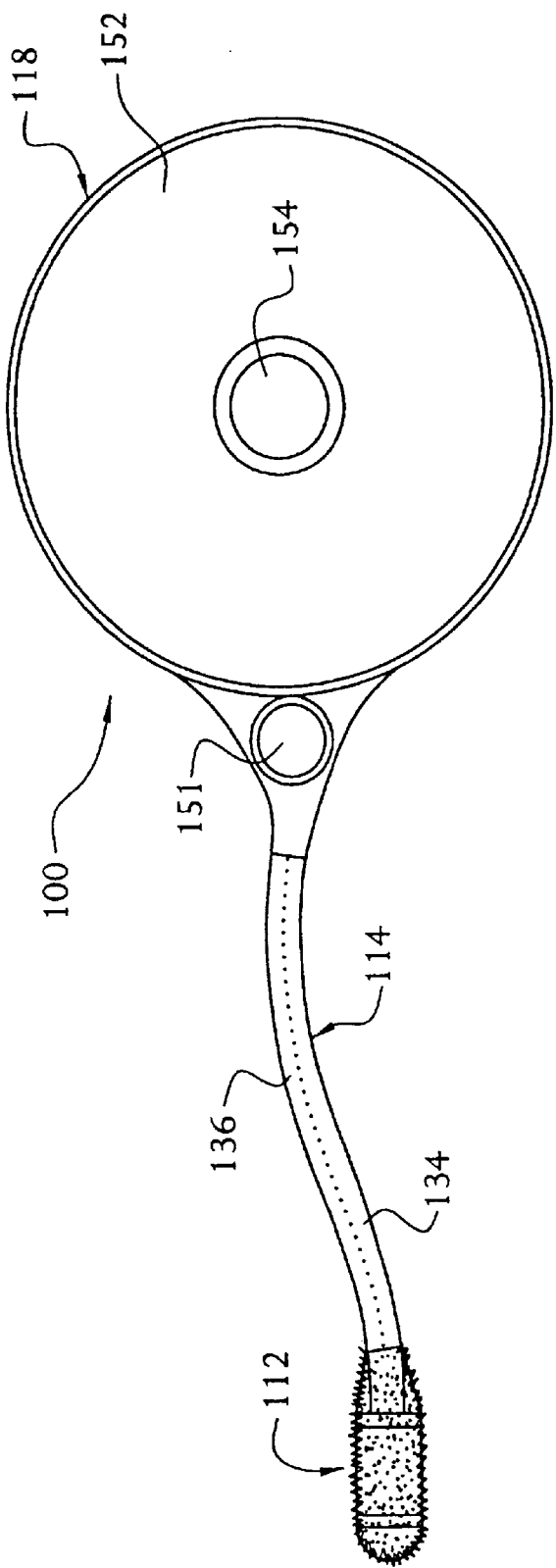
FIG. 8 illustrates an alternate embodiment of an implantable drug delivery catheter device according to the present invention.

FIG. 8 illustrates an alternative embodiment of the drug delivery catheter system 100 according to the present invention that includes an implantable drug feed device 118 that is connected to the drug delivery device 112 by a dual lumen catheter 114. An internal pump 152 supplies the drug to the drug delivery catheter 112 along a first lumen 134. A second catheter 136 connects the drug delivery device 112 with a flush port 151 formed on the implantable drug feed device 118. Cleaning of the pump mechanism and catheter system is conducted by placing a needle percutaneously in the pump's side flush port 151 while simultaneously providing an infusion of saline, detergent, or enzymatic cleaning solution.

Figure 9:
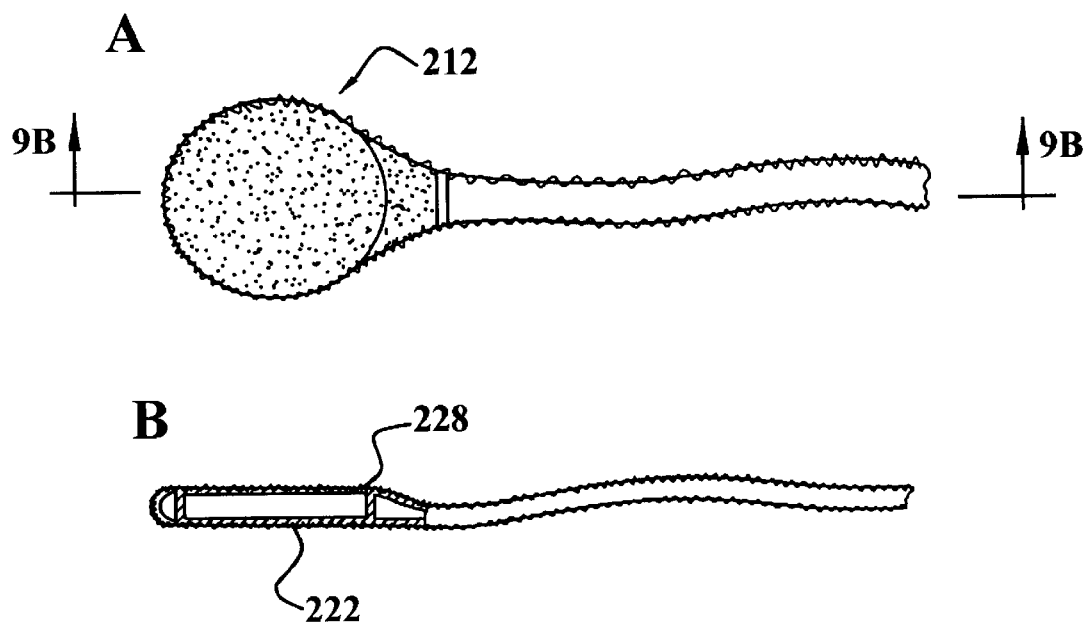
FIG. 9A is a top view of another embodiment of the implantable drug delivery catheter device.
FIG. 9B is a cross-sectional view of the implantable drug delivery catheter device of FIG. 9A.

FIGS. 9A and 9B depict an alternative embodiment of the drug delivery device 212. In this embodiment, the support structure 222 is in the shape of a flattened oval or disk and is covered with the tissue engineered capillary interface 228. The shape of the support structure 222 results in the drug delivery device 212 having a low profile for implantation between fascial or tissue planes. In this, as well as any other disclosed embodiments, the capillary interface 228 can be localized to one side of the device to direct drug delivery, if so desired. For example, implantation below the fascia of the rectus muscle and above the parietal peritoneum would provide an ideal location to direct drug to the highly vascular peritoneal membrane.

Figure 10:
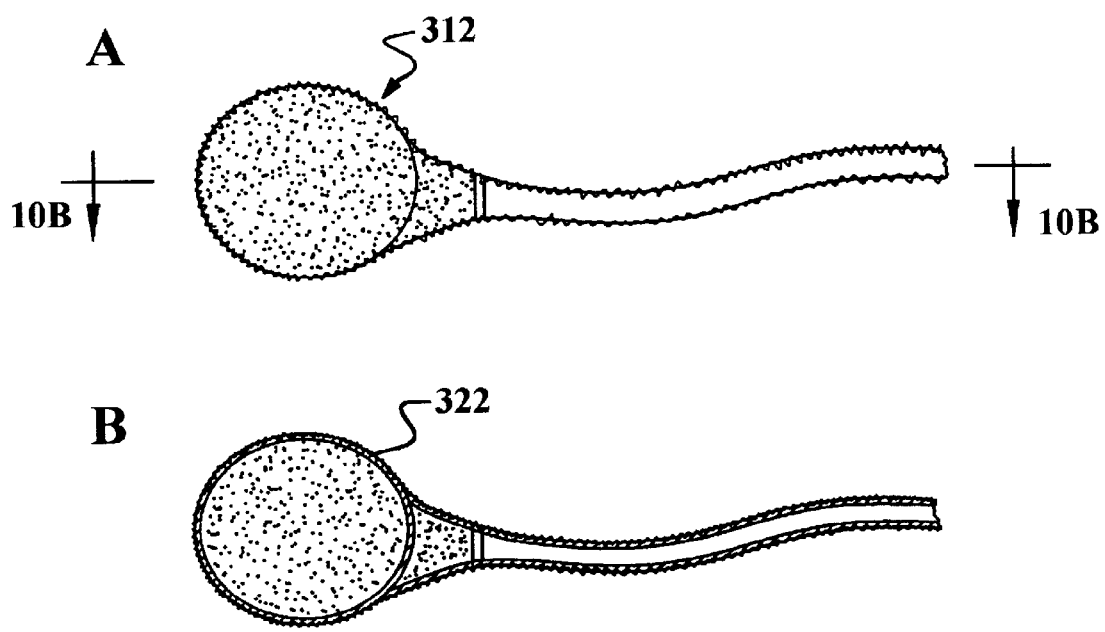
FIG. 10A is a top view of another embodiment of the implantable drug delivery catheter device.
FIG. 10B is a cross-sectional view of the implantable drug delivery catheter device of FIG. 10A.

FIGS. 10A and 10B depict another embodiment of the drug delivery device 312. In this embodiment, the support structure 322 is in the shape of a sphere or egg.

Figure 11:
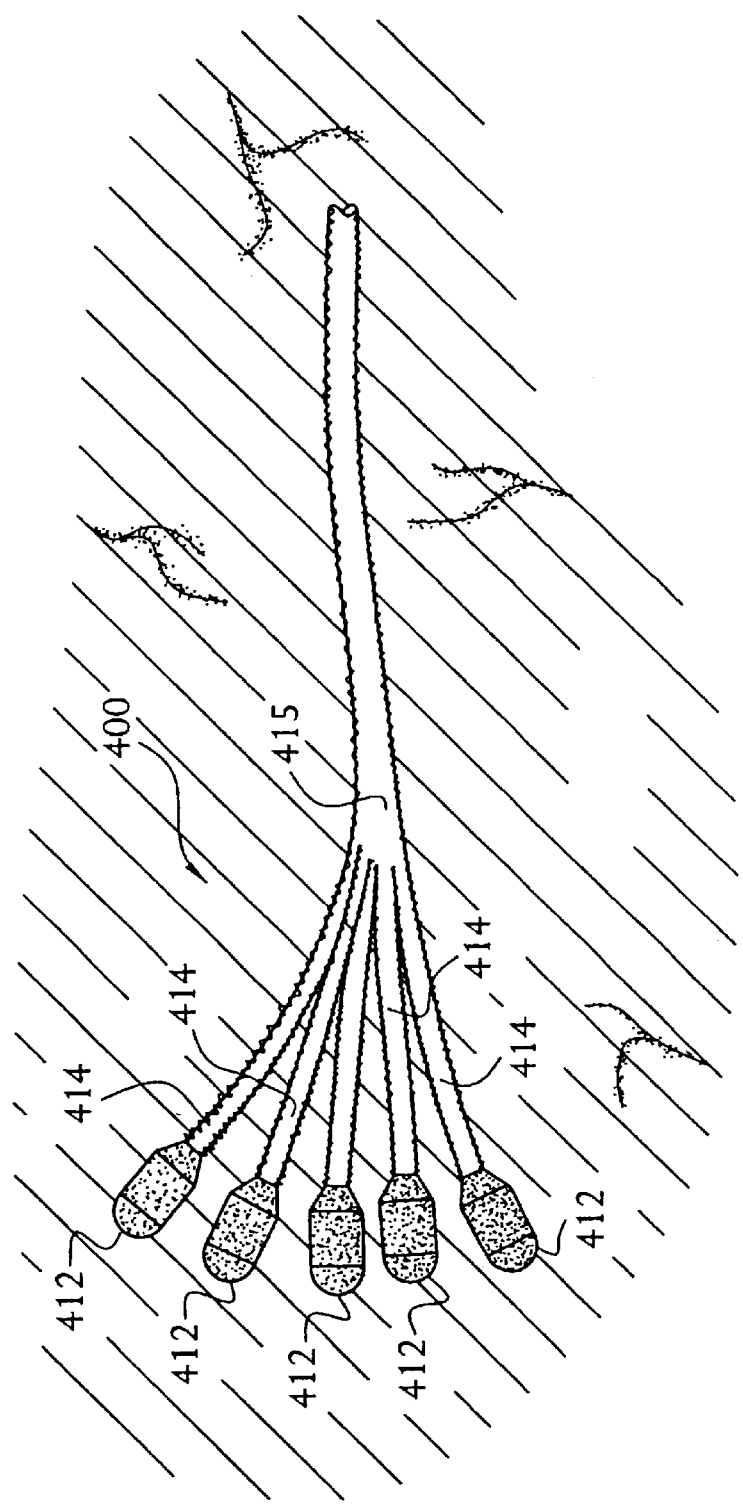
FIG. 11 illustrates another embodiment of the present invention which includes multiple implantable drug delivery devices.

FIG. 11 depicts an alternate embodiment of the invention 400 which includes a plurality of drug delivery devices 412, each delivery device 412 attaching to one end of a catheter 414. The opposite end of the catheters 414 is connected to a main catheter 415. This embodiment of the invention permits direct drug delivery with multiple tissue interfaces.

Figure 12:
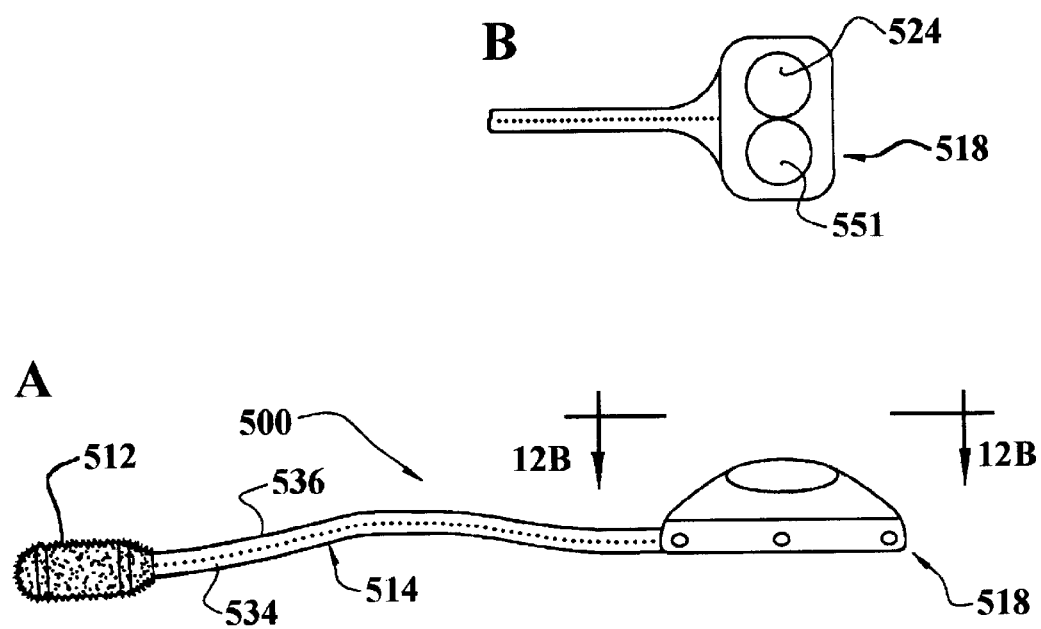
FIG. 12A is a side view of an alternate embodiment of the implantable drug delivery catheter device.
FIG. 12B is a partial top view of the implantable drug delivery catheter device of FIG. 12A.

FIGS. 12A and 12B depict a further embodiment of the present invention 500 illustrating an implantable double port subcutaneous infusaport 518. Drug is infused from the storage reservoir 554 of the infusaport using an external drug pump with percutaneous needle. The drug travels to the drug delivery device 512 via a first lumen 534 in a catheter 514. A second lumen 536 in the catheter 514 provides fluid communication between the drug delivery device 512 and a flush port 551 on the infusaport 518. Cleaning of the catheter system is conducted by placing a needle percutaneously in the flush port 551 while simultaneously providing an infusion of saline, detergent, or enzymatic cleaning solution down the primary drug infusion lumen 534.

Figure 13:
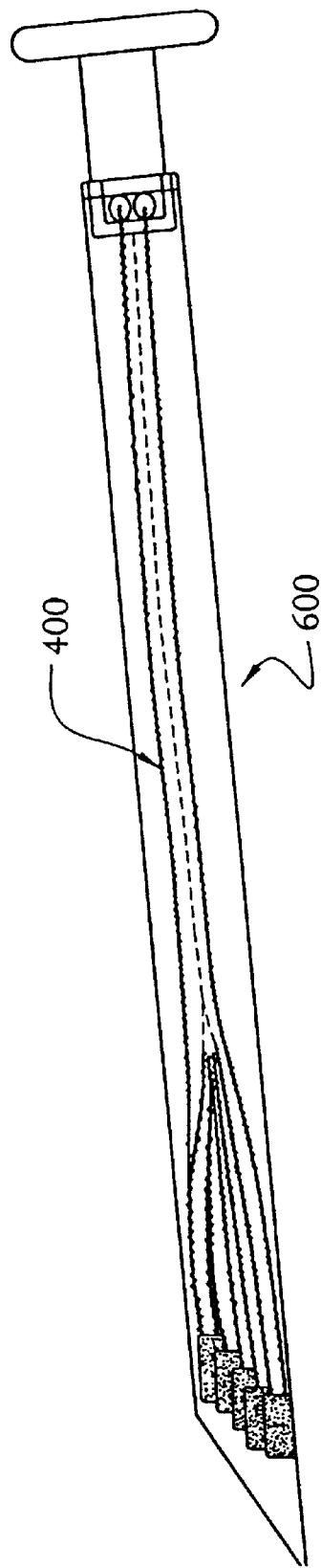
FIG. 13 illustrates a needle-like introducer for implantation of the catheter system according to the present invention.

FIG. 13 depicts a needle-like introducer 600 for percutaneous or laparoscopic implantation of the catheter system within connective tissue. The multiple drug delivery catheter system 400 of FIG. 8 is shown loaded within the introducer 600, ready for minimally invasive implantation.

The engineering and biomaterials selection of the drug delivery device described above enable tissue growth onto the device to form a capillary interface with minimal inflammation and encapsulation of tissue, thus reducing the thickness of the surrounding layers. Since mammalian tissues are organized into 3 dimensional structures, the membrane scaffolding architecture of this device optimizes structural and nutritional conditions needed for long-term use and functionality of the implant.

More specifically, the engineering of a three-dimensional scaffold with an interconnecting pore structure promotes tissue growth and neovascularization within and around the delivery device. Because the uniquely engineered capillary interface (three-dimensional single, bi-layer or multi-layer membrane) is immediately adjacent to the drug reservoir, the present invention provides more rapid uptake of a drug into the circulation due to the close proximity of the capillaries to the drug.

The size, shape, and membrane characteristics of the drug delivery device can be optimized to the type of tissue at the site of implantation. Such optimization maximizes the capillary density immediately adjacent to the inner membrane.

The ability to locate the drug delivery device catheter system within the loose connective tissue of the subcutaneous space provides systemic drug absorption, while implantation within the loose connective tissue of the bowel mesentery provides direct absorption into the portal venous system. Implantation sites for the drug delivery device catheter system include abdominal, subcutaneous, and peritoneal tissues, the brain, the intramedullary space, and other suitable organs or body tissues.

As discussed above, the drug delivery device catheter system may be incorporated with an external or implantable infusion pump to optimize drug delivery and physiologic parameters, such as, but not limited to, insulin delivery in diabetics. The clinical applications of this device include insulin delivery, or other hormone therapy, chemotherapy, gene therapy, antibiotic therapy, and chronic pain. This device may be used in the treatment of or as a therapeutic modality in disease categories not limited to vascular, endocrine/metabolic, cardiac respiratory, renal, neoplastic, CNS/psychiatric, gastrointestinal, chronic pain, bone and joint, hematological, or autoimmune diseases, or any diseases or disorders requiring continuous achievement of therapeutic drug levels, where titration is necessary to respond to the dynamic physiological condition of a human or animal.

While the present invention has been described as including a drug delivery device in addition to a catheter, it is also contemplated that a portion of the catheter may be perforated and covered with the outer and inner membrane layers. Thus, the catheter 14 would operate as the drug delivery device with the perforated portion of the catheter acting as the support structure for the drug delivery device.

Figure 14:
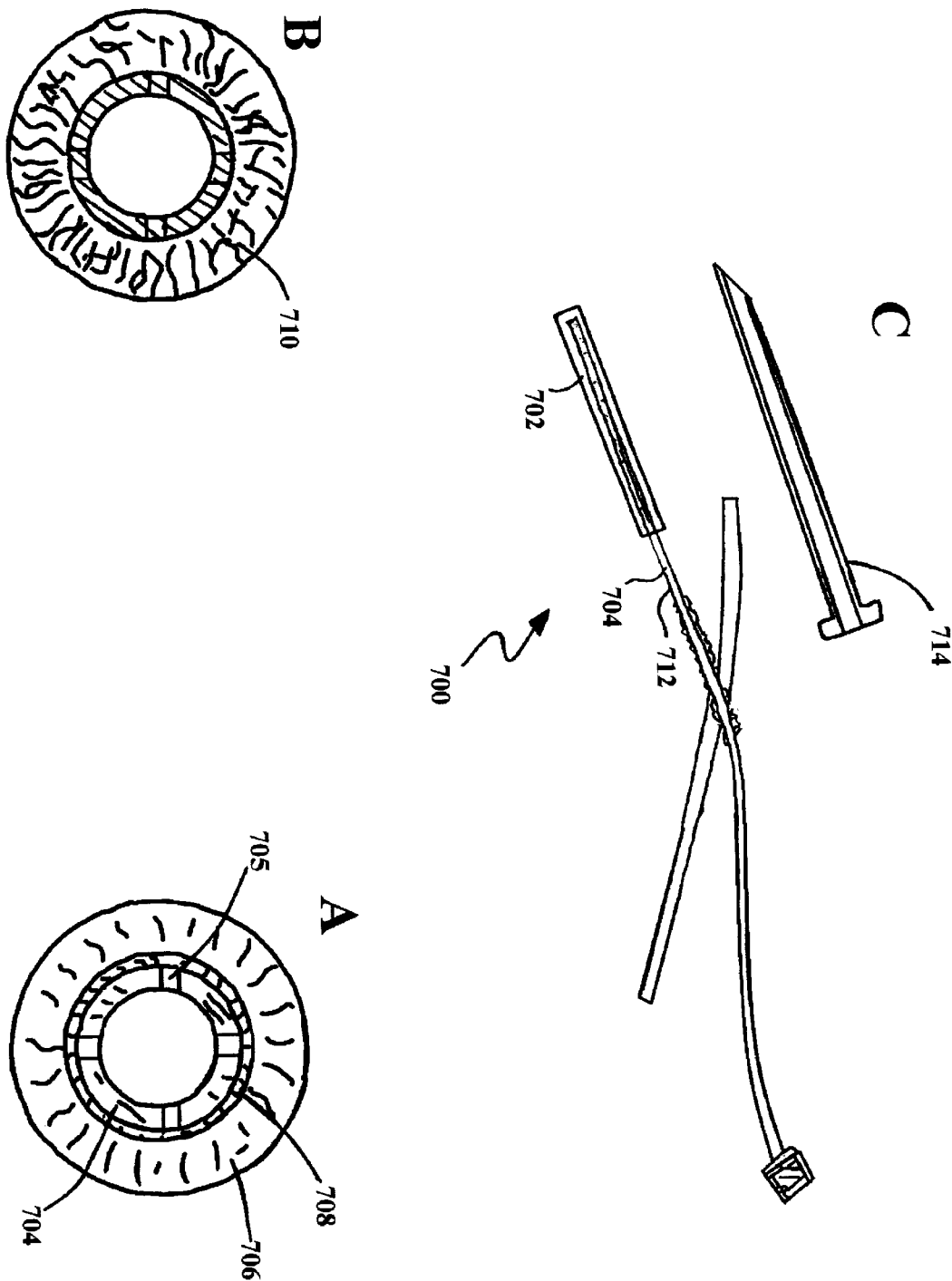
FIG. 14 illustrates an alternate embodiment of the invention for use in non-permanent installation of a drug delivery catheter according to the present invention.
Figure 15:
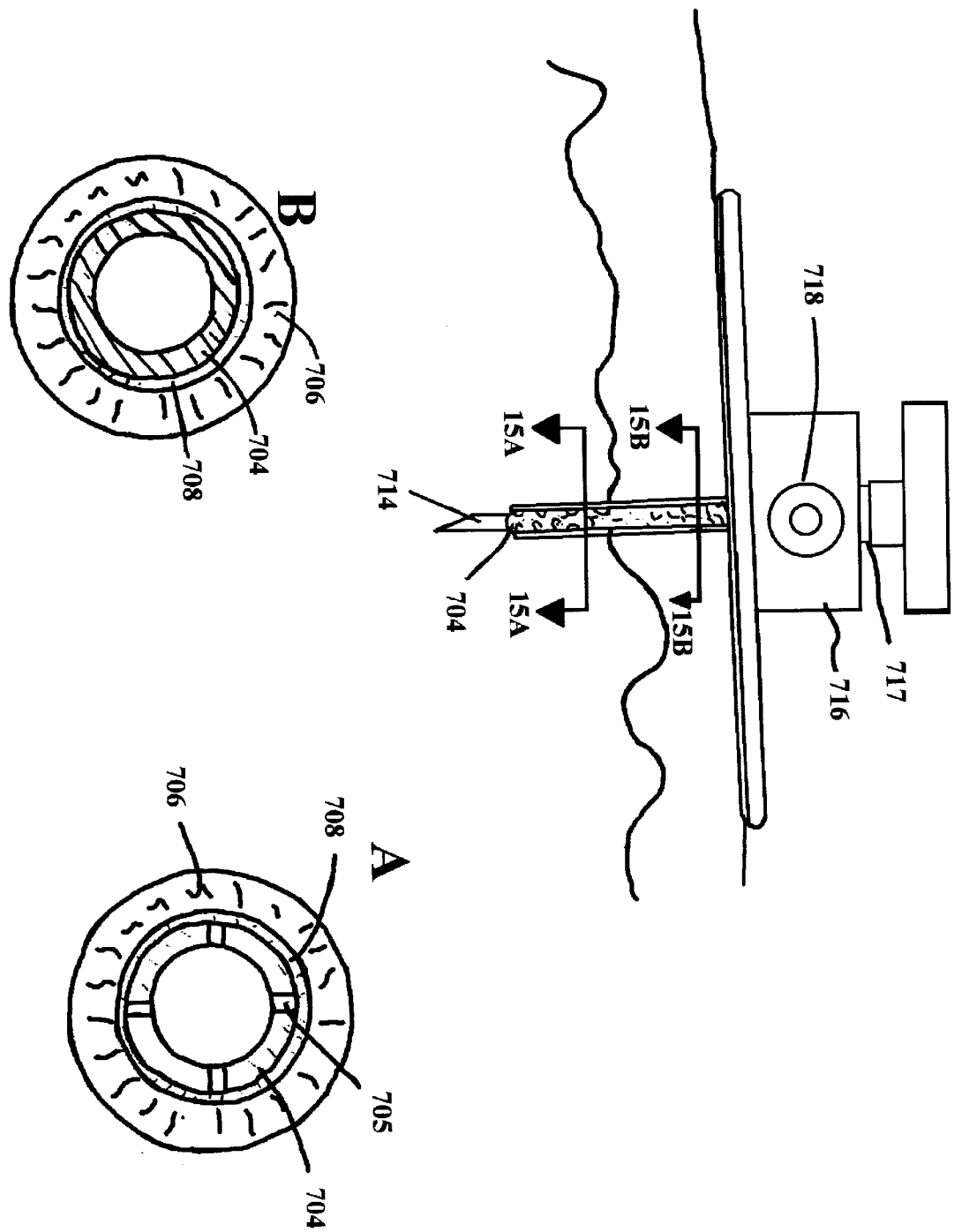
FIG. 15 is a variation of the drug delivery catheter of FIG. 14.

An alternate embodiment of the invention is shown in FIGS. 14–15. In this embodiment the drug delivery catheter system 700 is designed for placement within a patient. The system shown in FIG. 14 is a modified version of the system discussed in detail above. The primary difference is the elimination of the separate capillary interface drug delivery device and, instead, incorporating the membrane technology into a disposable catheter. In this illustrated embodiment, the capillary interface 702 is incorporated directly into the catheter 704. More particularly, a distal portion the catheter 704 is the support structure that supports the capillary interface 702 and serves as the drug reservoir. The distal end of the catheter 704 has a series of perforations or orifices 705 formed about it that are designed to permit drug flow out of the catheter 704 and into the capillary interface 702. The catheter 704 is preferably a small diameter single lumen catheter constructed of a biocompatible flexible material, such as silicone, polyethylene or tetrafluoroethylene.

The capillary interface 702 forms a porous scaffold on the distal portion of the catheter 704 over the orifices. The capillary interface 702 is similar to the capillary interface described above and, in one embodiment, includes an outer membrane 706 formed about an inner membrane 708. The scaffold 702 can be made from many suitable materials, such as hydrogel, polymers, metals, ceramics and natural matrix compounds (e.g., collagen hyuronate, or fibronectin). The scaffold 702 is designed to promote and maintain the ingrowth of healthy vascular tissue with a high capillary density in close proximity to the drug delivery orifices. It is also contemplated that the scaffold 702 can be made from biodegradable material so as to permit the scaffold to remain within the patient after the catheter is removed.

If the membrane of the capillary interface 702 are made as a bilayer (FIG. 14a), then the inner or small pore membrane 708 preferably has pore diameters between about 10–1000 nanometers. As such, drug diffusion through the inner pores would be limited and only occur at a clinically significant rate during positive pressure infusion. The outer or large pore membrane 706 preferably has pore diameters between about 1–300 micrometers. The pores from the two layers are preferably diffusely interconnected. If the capillary interface 702 is made as a monolayer (FIG. 14b), then the pores 710 preferably taper between the pore diameter extremes.

Angiogenic growth factors and/or anti-inflammatory medication may be added to the scaffold 702 to promote the rapid ingrowth of tissue with high capillary density and minimal fibrosis.

In the specific case of insulin delivery, the scaffold 702 may be designed to optimize the local tissue environment for insulin dissociation into the monomeric form. Equilibrium between the monomeric-dimeric-hexameric insulin molecular forms is subject to the physiologic conditions in the subcutaneous tissue adjacent to the capillary wall. A scaffold that releases bicarbonate to maintain a raised interstitial tissue matrix (extracellular fluid) pH will increase the solubility of the insulin for more efficient diffusion to adjacent absorptive capillaries. Only monomeric insulin will be efficiently absorbed across the capillary wall because the endothelial pore size (2.0–3.0 nm) is close to that of the molecular radius of monomeric insulin (1.2 nm).

In order to optimize the adhesion of skin epithelial cells to the outer wall of the catheter 704, the outer surface 712 of the catheter in the non-capillary interface region is modified. A high degree of vascularity is desired to provide white blood cell penetration to phagocytize invading bacteria. Rapid epithelial cell adhesion and tissue penetration with a high vascularity will, therefore, minimize the risk of cutaneous infection. A porous extracellular matrix (e.g., collagen, fibrinogen, fibronectin, or hyaluronate with RGD ligands) or a porous catheter materials (e.g., silicone, ePTFE, hydrogel, DACRON) will promote suitable epidermis/dermis attachment to the catheter's outer wall.

The catheter 704 with the catheter interface 702 is designed to be inserted into the skin with the use of a needle introducer 714 (shown in FIG. 14c). The introducer 714 is a hollow, hard walled tubular device with a sharp tip designed to penetrate the skin. The introducer 714 is inserted into the skin with the catheter 704 inside it. The introducer can then be removed leaving the catheter 704 with the capillary interface 702 located within the skin.

The length of the capillary interface 702 and the catheter 702 can vary depending on the drug delivery site. Preferably the overall length of the subcutaneous portion of the catheter 702 and capillary interface is about 1–2 cm.

Patients may self-insert the small diameter percutaneous flexible catheter using the following method:

1) topical anesthesia is applied to the skin (EMLA Cream);
2) aseptic surface cleaning is performed;
3) the needle introducer is inserted at 30 degree angle into the skin, up to the hub;
4) the flexible catheter is inserted through needle introducer;
5) the needle introducer is removed, leaving flexible catheter in proper percutaneous location, proximal porous surface modification adjacent to skin epithelial cells and distal surface modification located in loose connective tissue of subcutaneous adipose tissue;
6) the base of the catheter is adhered to skin;
7) a Luer Lock connector and antibacterial filter are attached to the external portion of catheter; and
8) an external pump/tubing is attached to quick connect-disconnect portion of the percutaneous catheter system.

A variation on this alternative embodiment of the present invention is shown in FIG. 15. In this configuration, the catheter 704 is attached to a base 716 which has an needle entry port covered by a silastic diaphragm 717. The diaphragm 717 is self-closing in order to maintain a closed system. The entry port permits a needle introducer 714 to be inserted into the center of the catheter 704 prior to percutaneous insertion. In this embodiment, the introducer 714 is inserted into the catheter and the combination introduced into the skin. Following insertion, the needle introducer 714 is removed leaving the flexible catheter at the proper depth for subcutaneous drug delivery. A port 718 on the base 716 permits attachment of an external catheter.

As shown in FIG. 15a, the distal portion of the subcutaneous catheter has multiple orifices for drug delivery through the scaffold as described above. Hydrogel with angiogenic growth factors can be used in this portion of the catheter to facilitate capillary ingrowth. The catheter portion adjacent to the skin edge (FIG. 15b) is preferably surface modified and does not have perforations formed in the wall. Hydrogel with anti-inflammatory steroids and antibiotic medication can be used in this portion of the catheter to minimize inflammation and the risk of bacterial infection.

This alternate embodiment of the invention provides a non-permanent percutaneous drug delivery catheter system that minimizes the risk of cutaneous infection and facilitates rapid and controlled drug absorption into a human. The present invention increases the capillary surface area in close proximity to the catheter's drug delivery orifices eliminating the lag period (10 minutes) for the first insulin molecules to diffuse through the extracellular matrix to the capillary surface. The present invention provides for rapid absorption to eliminate the subcutaneous insulin depot and minimizes the time and variability to reach the maximum plasma insulin concentration (5–15 minutes versus 45–180 minutes with the CSII system). Also, the present invention eliminates the subcutaneous depot so as to limit the absorption of insulin following stoppage of the external infusion pump (rapid offset of insulin absorption). Furthermore, the increased capillary density adjacent to the catheter will significantly decrease the risk for cutaneous infection by providing a means of transportation of macrophages and neutrophils (white blood cells) at the interface of a foreign body and tissue.

The system described above provides a local tissue environment (neutral rather than acidic pH, lower insulin tissue concentration) that promotes the dissociation of dimeric and hexameric molecular insulin into the monomeric form, thereby improving absorption. Also, the system decreases the risk for cutaneous infection by promoting epithelial cell adhesion with vascularity at the epidermis/dermis/catheter interface.

Although the invention has been described and illustrated with respect to the exemplary embodiments thereof, it should be understood by those skilled in the art that the foregoing and various other changes, omissions and additions may be made therein and thereto, without parting from the spirit and scope of the present invention.

In Vivo Data

The objective of the in vivo investigation was twofold: 1. To demonstrate tissue ingrowth and long-term maintenance of a capillary interface within the large pore structure (10–20 $\mu$m) of a newly engineered hydrogel, and 2. To demonstrate feasibility of rapid insulin delivery, via this hydrogel, after a 5-month implantation period in rats.

Methods

The PHEMA sponges used for these studies were synthesized at Drexel University in Dr. Lowman's laboratory. The sponges were caste into 12 mm×1 mm cylinders and had an average pore diameter of 7.66 $\mu$m. The center of the wet sponges was lanced with a 23-gauge-punching device to allow insertion of the catheter tubing into the hydrogel structure. The hydrogel was subsequently fixed onto the catheter tubing (L=10 cm) at the entry point using surgical grade silicone adhesive (Silastic, Dow Corning) and the entire device sterilized in ethelyne oxide.

The devices were implanted in 4 rats weighing ~350 gm. Each animal was implanted with 2 devices: a mesenteric DDCS, implanted within the loose connective tissue of the bowel mesentery, and a subcutaneous DDCS implanted in the dorsal subcutaneous loose connective tissue. Catheters were primed with saline and proximal ends sealed. Catheters were then coiled and secured within the abdominal and subcutaneous spaces, respectively. There were no perioperative surgical complications and all 4 animals increased to a mean weight of 592±83 gm by 20 weeks.

The proximal portion of the catheters was exteriorized at 20-weeks post implantation and human insulin infusions were started at 10 milliU/kg/min with infusion rates of 60 μL/hr after careful determination of catheter dead space volume. Two animals were randomly assigned to receive insulin via mesenteric DDCS and two animals received infusions via subcutaneous DDCS. Insulin and glucose concentrations were measured at 5, 15, and 30 min post infusion and data are presented in FIGS. 9 and 10. When the infusion was terminated, depth of anesthesia was increased and DDCS and surrounding tissue were explanted and immediately immersed in 10% buffered formalin for histological analysis. Tissue specimens were embedded in paraffin and 7–10 microns sections were prepared for H and E stains.

Results

Figure 16:
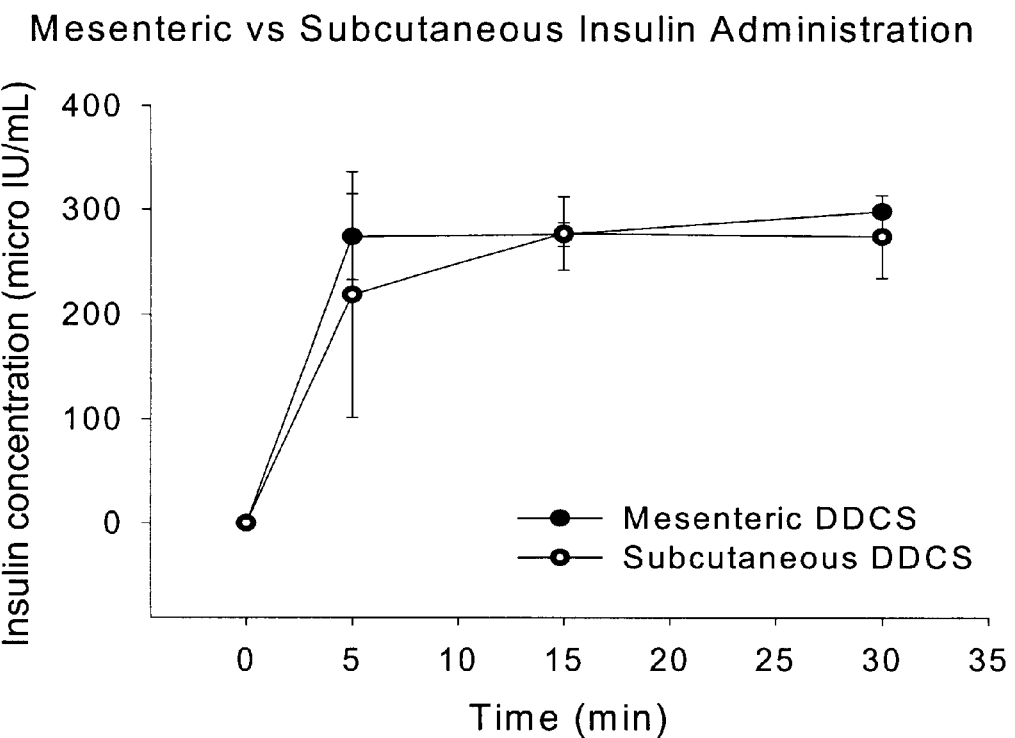
FIG. 16 is a graph comparing mesenteric and subcutaneous insulin administration in rats with implanted drug delivery catheters. Plasma concentration of human insulin infused into rat at 10 mU/kg/min is shown versus time.
Figure 17:
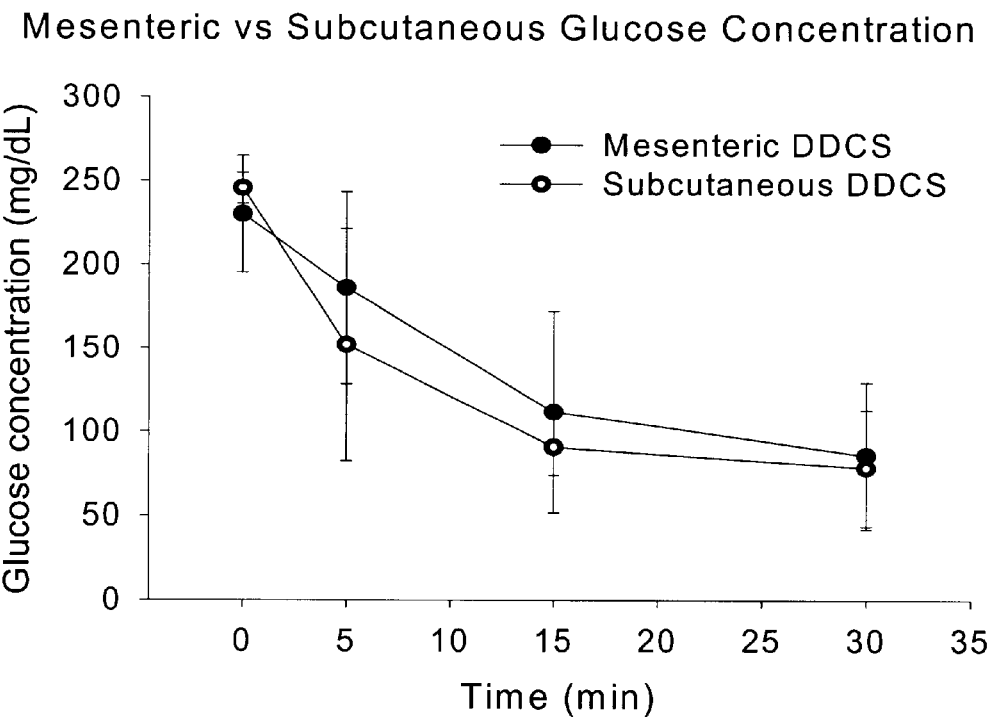
FIG. 17 is a graph comparing mesenteric and subcutaneous glucose concentration in rats infused with insulin as shown in FIG. 16. Plasma concentration of glucose in rats infused as described in FIG. 16 is shown versus time.
Figure 18A:
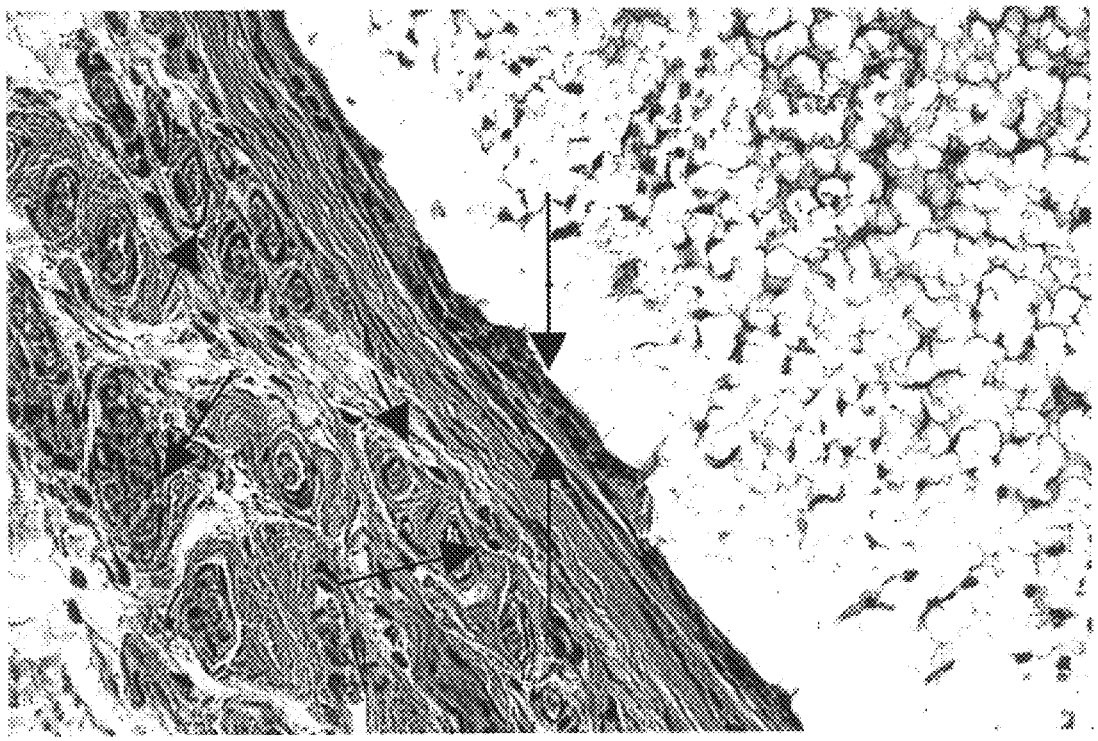
FIG. 18 is a series of photographs of four histological sections of implants and surrounding tissues demonstrating normal tissues with no evidence of inflammation or encapsulation in rats with implanted drug delivery catheter systems. The histological sections of implants and surrounding tissues (FIG. 18, Panels a–d) are as follows: a) Mesentery PHEMA×400; b) Mesentery×400; c) Subcutaneous×100; and d) Subcutaneous×400.
Figure 18B:
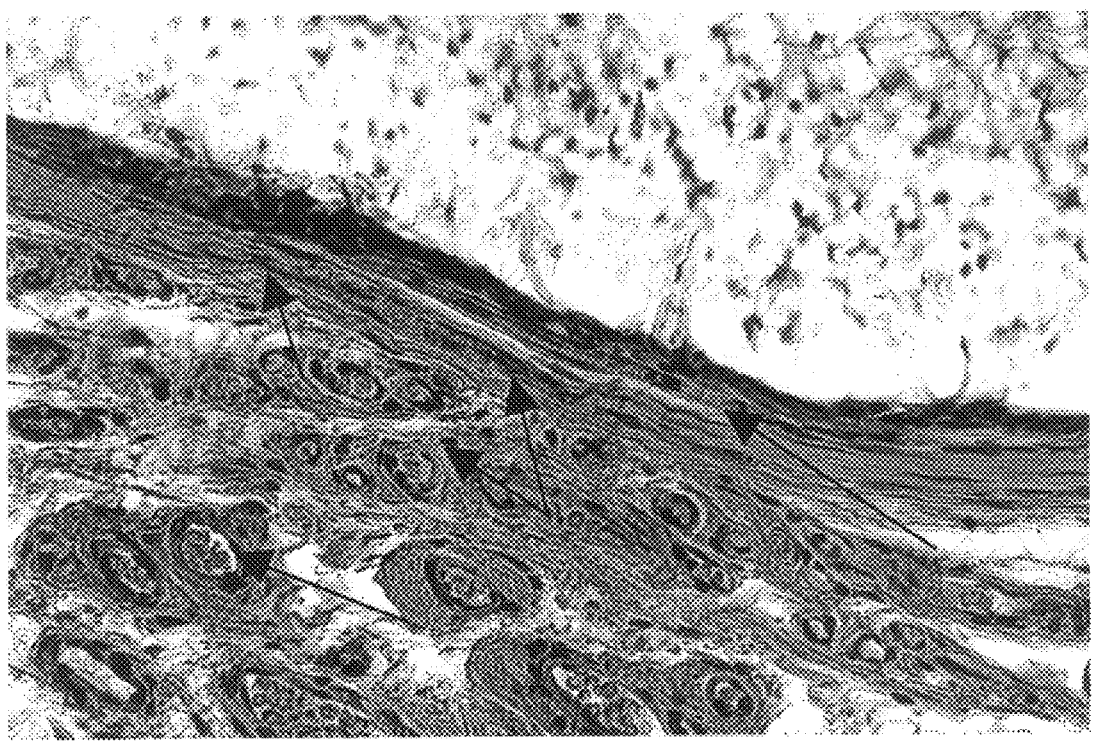
Figure 18C:
Figure 18D:
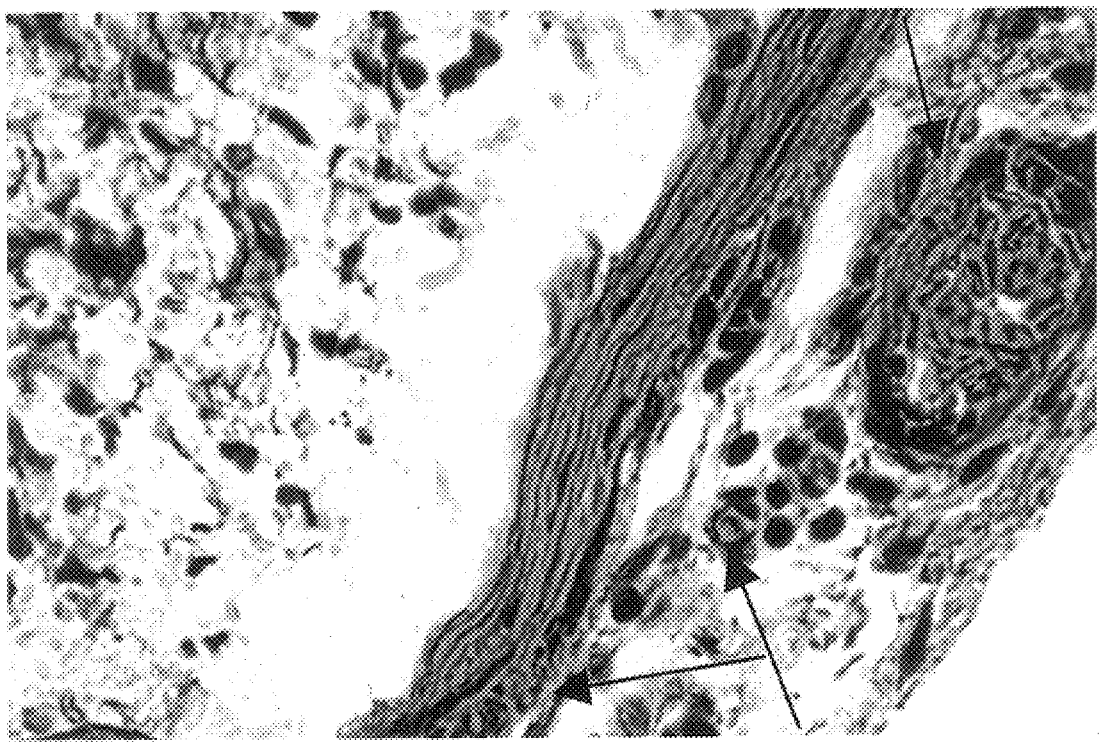

Blood insulin levels peaked by 5-min post infusion and remained elevated for the duration for both mesenteric and subcutaneous infusions (FIG. 16). Blood glucose concentrations decreased in proportion to increasing insulin concentrations (FIG. 17). The high baseline glucose levels are attributable to a combination of the animals not having been fasted prior to the experiment, and the known effects of isoflurane anesthesia (suppression of endogenous insulin production). Glucose infusions were not needed under this experimental protocol which was of short duration and involved non-survival surgery.

On explant of both subcutaneous and intraperitoneal catheters, gross examination of surrounding tissues appeared normal with no evidence of inflammation or encapsulation. Histological sections of implants and surrounding tissues (FIG. 18, Panels a-d.) supported these observations revealing little to no white blood cell infiltration peripheral to the hydrogel and only a thin (10–35 μm) connective tissue boundary (CTB) adjacent to the hydrogel. The CTB was richly vascularized but with the methods used it was not possible to quantify the extent of vascularization into the gel scaffold. Numerous capillaries of varying sizes can be seen on each panel as well as capillaries along the CTB (panel b).

Conclusions

These results demonstrate that our large pore PHEMA hydrogel formulation possess the necessary properties for tissue ingrowth and the maintenance of vascular structures for insulin delivery. These clearly point to the achievement of rapid insulin delivery via a large pore biomaterial-tissue interface.

What is claimed is:

1. A drug delivery device for use in a drug delivery system to deliver drugs to a prescribed location within a mammal, the drug delivery device adapted for implantation into the mammal, the drug delivery device comprising:
    a support structure adapted for implantation into a mammal and adapted to receive a flow of drugs, the support structure having a plurality of holes formed therein for permitting drugs to flow out of the support structure and into the mammal; and
    a capillary interface disposed about the support structure, the capillary interface including an outer portion which is adapted to facilitate the ingrowth of vascular tissue, and an inner portion which is adapted to inhibit the ingrowth of vascular tissue while permitting the flow of drugs from the support structure out through the capillary interface.

2. The drug delivery device of claim 1 wherein the outer and inner portions of the capillary interface each include a layer of porous biomaterial, and wherein the pore cell size of the outer layer is larger than the pore cell size of the inner layer.

3. The drug delivery device of claim 2 wherein the pore cell size of the outer layer is between about 0.02 μm and about 300 μm and wherein the pore cell size of the inner layer is between about 0.01 μm and about 0.8 μm.

4. The drug delivery device of claim 1 wherein the capillary interface includes tapering elements which are supported by the support structure, each tapering element having a first diameter at an outer end which forms the outer portion of the capillary interface, and a second diameter at its inner end which forms the inner portion of the capillary interface, the first diameter being larger than the second diameter.

5. The drug delivery device of claim 1 wherein the support structure includes a perforated shell that defines a drug reservoir, and wherein a drug port permits passage of drugs into the drug reservoir.

6. The drug delivery device of claim 5 wherein the perforated shell is substantially cylindrical in shape, and wherein the support structure further includes smooth perforated shaped ends on the shell, the drug port extending out from one of the ends.

7. The drug delivery device of claim 1, wherein the device is part of a drug delivery system, the delivery system including:
    a catheter attached to the support structure; and
    a drug feed device attached to the catheter, the drug feed device including a drug supply and a pump, the pump adapted to produce a positive pressure flow of drugs out of the drug supply, through the catheter and into the drug reservoir.

8. The drug delivery device of claim 7, wherein the drug feed device includes a processor for titrating the delivery of drugs.

9. The drug delivery device of claim 7, wherein the catheter is a dual lumen catheter with both catheters communicating with the drug delivery device.

10. The drug delivery system of claim 1 wherein the perforated support housing is a perforated portion of a catheter.

11. An implantable drug delivery device for use in a drug delivery system to deliver drugs to a location under a mammal's skin, the drug delivery device comprising:
    a perforated support housing defining a drug reservoir, the housing adapted to receive a flow of drugs from a drug supply, the housing having a plurality of holes formed in it; and
    a capillary interface disposed about the housing, the capillary interface including an outer layer of porous biomaterial which is adapted to facilitate the ingrowth of vascular tissue, and an inner layer of porous biomaterial which is adapted to inhibit the ingrowth of vascular tissue while permitting a flow of drugs to pass from the drug reservoir through the plurality of holes and out through the capillary interface.

12. The drug delivery device of claim 11 wherein the pore cell size of the outer layer is between about 0.8 μm and about 300 μm and wherein the pore cell size of the inner membrane is between about 0.01 μm and about 0.8 μm.

13. The drug delivery device of claim 11 wherein the perforated shell is substantially cylindrical in shape, and wherein the support structure further includes smooth perforated shaped ends on the shell, the drug port extending out from one of the ends.

14. The drug delivery system of claim 11 wherein the perforated support housing is a perforated portion of a catheter.

15. A drug delivery system for delivering drugs to a location under a mammal's skin, the drug delivery system comprising:
   a drug feed device including a drug supply and a pump, the pump adapted to produce a positive pressure flow of drugs out of the drug supply;
   a catheter having at least one lumen in fluid communication with the feed device for receiving a flow of drugs, a portion of the catheter adapted disposed under the skin of a mammal;
   a drug delivery device adapted to be mounted under the skin of a mammal, the drug delivery device including:
      a support structure forming a drug reservoir, the support structure having a drug port on it which is attached to the catheter and provides fluid communication between the lumen in the catheter and the drug reservoir, the support structure having openings which permit drugs to flow out from the drug reservoir and into the mammal; and
      a capillary interface disposed about the support structure, the capillary interface including an outer membrane pore structure which is adapted to facilitate the ingrowth of vascular tissue, and an inner membrane pore structure which is adapted to inhibit the ingrowth of vascular tissue while permitting the flow of drugs from the support structure out through the capillary interface, the outer and inner membrane pore structures including a plurality of pores, the pores on the outer membrane pore structure being substantially aligned with the pores on the inner membrane pore structure.

16. The drug delivery system according to claim 15 wherein the drug delivery device further includes a processor for titrating the delivery of drugs by controlling the operation of the pump.

17. The drug delivery system according to claim 15 wherein the catheter is made from biomaterial to permit percutaneous surgical implantation under the skin of a mammal.

18. The drug delivery system according to claim 15 wherein the drug feed device is permanently implanted within the mammal and the pump is a drug infusion pump.

19. The drug delivery system according to claim 15 wherein the drug delivery device and a portion of the catheter are implanted at a location selected from a group consisting of a subcutaneous space, fascia, muscle, mesentery, abdominal viscera, parietal peritoneum, peritonea cavity, serous membrane lined body cavity and solid organs.

20. The drug delivery system of claim 15 wherein the outer and inner membrane pore structures are made from material selected from at least one of the group consisting of hydrogels, poly (2-hydroxyethyl methacrylate, pHEMA), hydroxyethyl methacrylate (HEMA), polyacrylonitrile-polyvinyl chloride (PAN-PVC), polymers, polytetrafluoroethylene (PTFE), expanded polytetrafluoroethylene (ePTFE), polypropylene, high density polyethylene, polyurethane, polyester (Dacron), polyvinyl chloride, polyvinyl alcohol, acrylic copolymers, polysulfone, nylon, polyvinyl diflouride, polyanhydrides, silicone, polycarbonate, cellulose acetate, mixed ester cellulose, collagen, fibrin, poly(1-lysine), poly (L-lactic acid), hydroxyethylmetharcrylate, protein polymers, peptides polymers, hydroxyapetite alumina, zirconia, carbon fiber, aluminum, calcium phosphate, titanium, titanium alloy, nintinol, stainless steel, and CoCr alloy.

21. The drug delivery system of claim 15 wherein the outer and inner membrane pore structures include interstitial tissue matrix substances selected from a group consisting of polyethylene oxide (PEO), collagens, laminins, fibronectins, proteoglycans, vitronectins, fibrin, albumin, tissue growth factors, angiogenic growth factors, anti-inflammatory medications and rejection medications.

22. The drug delivery system of claim 15 wherein the support structure is substantially oval-sbaped.

23. The drug delivery system of claim 15 wherein the reservoir is disc-shaped.

24. The drug delivery system of claim 23 wherein the openings are distributed on one side of the device for directional tissue drug delivery.

25. The drug delivery system of claim 15 wherein the support structure forms a drug reservoir with a volume between about 0.10 microliters and about 5 milliliters.

26. The drug delivery system of claim 15 wherein the pore size of the inner membrane pore structure is between about 0.01 micrometers and about 0.8 micrometers.

27. The drug delivery system of claim 15 wherein the thickness of the inner membrane pore structure is between about 2 micrometers and about 150 micrometers.

28. The drug delivery system of claim 15 wherein the pore size of the outer membrane pore structure is between about 0.8 micrometers and about 300 micrometers.

29. The drug delivery system of claim 15 wherein the thickness of the outer membrane pore structure is between about 10 micrometers and about 5000 micrometers.

30. The drug delivery system of claim 15 wherein the preferred porosity of the outer membrane pore structure is between about 70 percent and about 95 percent.

31. A drug delivery catheter system for implantation within the body of a mammal, comprising a drug delivery catheter system implantated at a preferred anatomic location for targeted drug absorption; said drug delivery catheter system adapted to precisely control the dose of drug delivered to an immediately adjacent vascular tissue and adapted to promote and maintain a high capillary density within the adjacent vascular tissue, said system providing rapid and controlled drug absorption kinetics targeted to a preferred tissue.

32. The drug delivery catheter system of claim 31, further comprising:
   a flexible drug delivery catheter with a drug delivery channel, adapted for implantation within a mammal, further adapted to receive a flow of drug from an infusion pump or syringe, and direct the flow of drug to a preferred vascular tissue, the catheter delivery channel having a proximal end for efficient coupling to the source of drug, and a distal end having a plurality of holes permitting the outward flow of drug into the vascular tissue;
   a support structure drug reservoir, connected to and adapted to receive a flow of drug from the distal end of the catheter delivery channel, said support structure drug reservoir having a plurality of holes to permit the flow of drug out of the support structure into the vascular tissue;

a small pore inner membrane structure, adapted to adhere to the support structure, the inner membrane structure having a preferred pore size, thickness, and chemical composition to provide a controlled rate of outward drug diffusion, said inner membrane further adapted to maintain an open pore structure by inhibiting the adhesion and ingrowth of cells and extra cellular components, thereby permitting the controlled and directional flow of drug from the support structure into the vascular tissue; and an outer membrane with a larger interconnecting pore structure, adapted to adhere to and interconnect with the small pore inner membrane, said outer membrane further adapted to optimize the ingrowth and maintenance of vascular tissue within the pore structure and to optimize capillary growth immediately adjacent to the small pore inner membrane, thereby permitting drug to flow from the support structure reservoir, through the inner membrane, to the immediately adjacent vascular tissue.

33. The drug delivery catheter system of claim 32, wherein the pore size, thickness, and chemical composition of the small pore inner membrane structure limits the outward passive diffusion of drug from the reservoir, with flow through the inner membrane precisely controlled by the pressure differential across the membrane, the pressure differential produced by a drug infusion pump or syringe.

34. The drug delivery catheter system of claim 32, wherein the preferred pore size of the inner membrane is between 100 Angstroms to 0.8 Micrometers.

35. The drug delivery catheter system of claim 32, wherein the preferred thickness of the inner membrane is between 0.5 micrometers and 150 micrometers.

36. The drug delivery catheter system of claim 32, wherein the pore size, membrane thickness, chemical composition, charge density, and surface texture of the inner membrane are optimized to maintain an open pore structure by inhibiting cell and protein adhesion.

37. The drug delivery catheter system of claim 32, wherein the inner membrane pore structure completely interconnects with the pore structure of the outer membrane.

38. The drug delivery catheter system of claim 32, wherein the inner membrane and outer membrane are constructed of the same material with a tapering pore structure, larger pore openings located within the outer region, smaller pore structures located within the inner region, with total interconnectivity of the pores.

39. The drug delivery catheter system of claim 32, wherein the pore size, membrane thickness, chemical composition, charge density, surface texture, ligand chemistry and density, and receptor chemistry and density of the outer membrane structure are optimized to promote cell adhesion, cell migration, extracellular matrix formation, and new blood vessel formation throughout the interconnecting pore structure; and are optimized to promote the ingrowth and maintenance of a healthy vascular tissue with a high capillary density, long-term within the interconnecting pore structure and in close proximity to the inner membrane.

40. The drug delivery catheter system of claim 32, wherein the support structure reservoir size, shape, material, hole size, method of manufacture, and method of surgical implantation are optimized to prevent failure and drug release when an outside traumatic force or excessive internal pressure are applied.

41. The drug delivery catheter system of claim 32, wherein the support structure reservoir is made from materials selected from at least one of the group of metals and metal alloys, plastic polymers, polyflurinated hydrocarbons, ceramics, and glasses.

42. The drug delivery catheter system of claim 32, wherein the support structure reservoir has a proximal end cap for attachment of the flexible drug delivery catheter and a distal end cap to produce an enclosed drug reservoir for implantation within the body of a mammal.

43. The drug delivery catheter system of claim 42, wherein the support structure reservoir has a proximal end cap with attached flexible catheter, a distal end cap, and one or more internal struts to optimize mechanical strength to prevent failure and drug release when an outside traumatic force or excessive internal pressure are applied.

44. The support structure reservoir of claim 41 wherein a laser is used to produce a plurality of holes of preferred size, geometric shape, and hole density.

45. The drug delivery catheter system of claim 32, wherein the support structure reservoir is constructed using MEMS and computer chip technology, providing a support structure surface with holes of preferred size, geometric shape, and hole density.

46. The support structure reservoir of claim 45, wherein the support structure reservoir is constructed using MEMS and computer chip technology, providing a support structure surface with holes of preferred size, geometric shape, and hole density, further providing a three dimensional structure with posts or mushroom-likw structures, having a variety of diameters, lengths, and geometric shapes located adjacent to the holes for mechanical attachment of the membrane to the uspport structure.

47. The drug delivery catheter system of claim 32, wherein the holes of the support structure line up with and connect with the pores of the inner membrane, permitting efficient flow of drug from the support reservoir to the vascular tissue.

48. The drug delivery catheter system of claim 32, wherein the hole size of the support structure reservoir is between 0.1 micrometer and 50 micrometers.

49. The drug delivery catheter system of claim 32, wherein the preferred thickness of the support structure reservoir is between 5.0 micrometers and 1000 micrometers.

50. The drug delivery catheter system of claim 32, wherein the preferred porosity or hole density of the support structure reservoir is between 30 and 90 percent.

51. The drug delivery catheter system of claim 32, wherein the support structure reservoir is substantially cylindrical in shape.

52. The drug delivery catheter system of claim 32, wherein the support structure reservoir is flattened with a disc or spoon-like shape with rounded edges.

53. The drug delivery catheter system of claim 32, wherein the holes or pores within the flattened support structure reservoir are distributed on one side for directional drug delivery to a preferred tissue.

54. The drug delivery catheter system of claim 32, wherein the preferred internal volume of the support structure reservoir is between 0.1 microliters and 5000 microliters.

55. The drug delivery catheter system of claim 32, wherein the shape of the support structure reservoir is substantially round or slightly oval.

56. The drug delivery catheter system of claim 32, wherein the support structure reservoir is a portion of the flexible drug delivery catheter with holes, pores, or perforations.

57. The drug delivery catheter system of claim 32, wherein the flexible drug delivery catheter is implanted across the skin of a mammal, with the distal portion of the flexible catheter attached to the support structure reservoir with associated membrane structures internal to the body, and the proximal portion of the flexible catheter external to the body of said mammal, the proximal end having a connector for attachment to an external syringe or drug infusion pump.

58. The drug delivery catheter system of claim 32, wherein the flexible drug delivery catheter, support structure reservoir and associated membranes are completely implanted within the body of a mammal with attachment of the proximal catheter portion to an implanted drug infusion pump or an implanted subcutaneous drug reservoir type device.

59. The drug delivery catheter system of claim 32, wherein the flexible drug delivery catheter is adapted to promote a mechanical adhesion between the catheter surface, the skin, and the subcutaneous tissue, the flexible catheter further adapted with porosity, surface chemistry, and surface texture, to optimize the adhesion of epithelial cells, fibroblasts, and extracellular matrix structural proteins to the biomaterial surface, thereby preventing the inward migration of epithelial cells, bacteria, and other skin pathogens.

60. The drug delivery catheter system of claim 59, wherein the mechanical adhesion between the catheter surface, the skin, and the subcutaneous tissues produces a physical and chemical barrier against the inward migration of epithelial cells, bacteria, and other skin pathogens.

61. The flexible drug delivery catheter of claim 59, wherein the region of the catheter adjacent to the skin and subcutaneous tissue is modified with an open interconnecting pore structure, the interconnecting pore structure having a diameter of 1 to 200 micrometers, constructed of natural materials with specific cellular and protein attachment receptors, or synthetic materials with surface chemistry, texture, and architecture, to optimize the adhesion and migration of cells and adhesion of extracellular matrix structural proteins to the catheter surface.

62. The flexible drug delivery catheter of claim 59, wherein the region of the catheter adjacent to the skin and subcutaneous tissue is made of natural materials with specific cellular attachment receptors and ligands and protein attachment receptors and ligands to optimize the adhesion of cells and extracellular matrix structural proteins to the catheter surface.

63. The flexible drug delivery catheter of claim 59, adapted with a flexible anchor disc and a cuff for implantation within the subcutaneous connective tissue layer, to optimize the mechanical adhesion of epidermal cells, fibroblasts, and extracellular matrix structural proteins to the biomaterial surface, the flexible anchor disc being of sufficiently large diameter to dissipate traction forces, thereby preventing the loss of adhesion between tissue elements and a biomaterial surface following patient movement and traction on the external portion of the catheter.

64. The drug delivery catheter system of claim 32, wherein the proximal portion of the flexible drug delivery catheter is adapted with an antibacterial filter that permits the free flow of drug but prevents bacteria from entering the drug delivery channel.

65. A non-permanent drug delivery catheter system for implantation across the skin of a mammal, adapted to promote growth of highly vascular tissue immediately adjacent to a drug delivery lumen without formation of a fibrous tissue capsule, the system providing rapid and controlled drug absorption kinetics targeted to the subcutaneous tissues, the drug delivery system comprising:

a flexible drug delivery catheter external to the body, with a drug delivery lumen, and a proximal connector for attachment to an insulin pump or syringe, a base platform for attachment to the external surface of the skin, adapted with a drug delivery lumen to permit the flow of drug from the lumen of the flexible drug delivery catheter, to the lumen of the support structure reservoir located within the subcutaneous tissues of the body, further adapted with a sharp tipped needle that penetrates a silastic membrane within the base and forms a stylet for percutaneous insertion of the support structure reservoir through the skin, a support structure having a plurality of holes to permit the flow of drug into the vascular tissues, a small pore inner membrane structure, adapted to adhere to the underlying support structure, the membrane structure having a pore size, thickness, and chemical composition to provide a controlled rate of outward drug diffusion, said inner membrane structure adapted to maintain an open pore structure by inhibiting adhesion and ingrowth of cells and extra cellular components, thereby permitting controlled and directional flow of drug from the support structure into the vascular tissue; and an outer membrane with a larger interconnecting pore structure, adapted to adhere to and interconnect with the pore structure of the inner membrane and adapted to optimize ingrowth of vascular tissue immediately adjacent to the small pores of the inner membrane, thereby permitting drug to flow from the support structure reservoir, through the inner membrane, to the immediately adjacent vascular tissue.

66. A non-permanent drug delivery catheter system for implantation across the skin of a mammal, adapted to promote the growth of highly vascular tissue immediately adjacent to a drug delivery lumen without the formation of a fibrous tissue capsule, the system providing rapid and controlled drug absorption kinetics targeted to subcutaneous tissues, the drug delivery system comprising:

a flexible drug delivery catheter with a drug delivery lumen, a portion located external and a portion located internal to the body of a mammal and, said flexible drug delivery catheter having a proximal connector for attachment to an insulin pump or syringe;

a support structure located internal to the body of said mammal, said support stucture having a plurality of holes to permit the flow of drug into the vascular tissues, a small pore inner membrane structure, adapted to adhere to the underlying support structure, the membrane structure having a pore size, thickness, and chemical composition to provide a controlled rate of outward drug diffusion, said inner membrane structure adapted to maintain an open pore structure by inhibiting adhesion and ingrowth of cells and extracellular components, thereby permitting controlled and directional flow of drug from the support structure into the vascular tissue; and an outer membrane with a larger interconnecting pore structure, adapted to adhere to and interconnect with the pore structure of the inner membrane and adapted to optimize ingrowth of vascular tissue immediately adjacent to the small pores of the inner membrane, thereby permitting drug to flow from the support structure reservoir, through the inner membrane, to the immediately adjacent vascular tissue.

67. A method of slow and controlled release of angiogenic growth factors from a pore structure of an outer membrane of a drug delivery catheter system implanted in mammal and designed to promote the ingrowth and maintenance of healthy tissue with a high capillary density, said system adapted to release angiogenic factors in a controlled fashion into the open pore structure of the outer membrane, thereby producing a concentration gradient to promote capillary growth throughout the pore structure and immediately adjacent to the inner membrane and providing controlled simultaneous release of at least one angiogenic factor.

68. A method of controlled delivery of angiogenic growth factor or factors from a drug infusion pump to a support structure reservoir of a drug delivery catheter system implanted in a mammal, said system providing a concentration gradient from an inner membrane of said system, to an outer membrane of said system, to surrounding internal tissue, said method of controlled delivery designed to promote rapid and sustained capillary ingrowth throughout a pore structure, the concentration gradient causing a high capillary density immediately adjacent to the inner membrane.

69. A method of delivering growth factors and tissue nutrients in a controlled fashion from a drug infusion pump of a drug delivery catheter system implanted in a mammal, to promote rapid and sustained capillary ingrowth and a healthy vascular tissue, on the surface and within the pore structure of a biomaterial, following implantation in a mammal.

* * * * *